US007867741B2

(12) United States Patent
Lopes Ferreira et al.

(10) Patent No.: US 7,867,741 B2
(45) Date of Patent: Jan. 11, 2011

(54) POLYPEPTIDES HAVING AN ACTIVITY IN THE MTBE DEGRADATION PATH AND USES THEREOF

(75) Inventors: Nicolas Lopes Ferreira, Raucourt (FR); Diane Labbe, Quebec (CA); Héléna Maciel, Porto (PT); Françoise Fayolle-Guichard, Clamart (FR); Frédéric Monot, Nanterre (FR); Charles W. Greer, Quebec (CA)

(73) Assignees: Institut Francais du Petrole, Rueil Malmaison (FR); Conseil National de Recherches du Canada, Ottawa, Ontario (CA)

( * ) Notice: Subject to any disclaimer, the term of this patent is extended or adjusted under 35 U.S.C. 154(b) by 0 days.

(21) Appl. No.: 11/996,127

(22) PCT Filed: Jul. 18, 2006

(86) PCT No.: PCT/FR2006/001758

§ 371 (c)(1),
(2), (4) Date: Jan. 18, 2008

(87) PCT Pub. No.: WO2007/010133

PCT Pub. Date: Jan. 25, 2007

(65) Prior Publication Data

US 2008/0210631 A1     Sep. 4, 2008

(30) Foreign Application Priority Data

Jul. 18, 2005   (FR)   .................................. 05 07577

(51) Int. Cl.
*C12N 9/02*     (2006.01)
*C12P 21/06*    (2006.01)

(52) U.S. Cl. ..................................... 435/189; 435/69.1
(58) Field of Classification Search ........................ None
See application file for complete search history.

(56) References Cited

PUBLICATIONS

Chica et al. Curr Opin Biotechnol. Aug. 2005;16(4):378-84.*
John T. Wilson, Ph.D., "Fate and Transport of MTBE and Other Gasoline Components", MTBE Remediation Handbook, pp. 19-61, 2004.
Jessica R. Hanson et al., "Biodergradation of Methy tert-Butyl Ether by a Bacterial Pure Culture", Applied and Environmental Microbiology, Nov. 1999, pp. 4788-4792.
Paul B. Hatzinger et al., "Biodergradation of Methy tert-Butyl Ether by a Pure Bacterial Culture", Applied and Environmental Microbiology, Dec. 2001, pp. 5601-5607.
Alan Francois et al., "Biodergradation of Methy tert-Butyl Ether and Other Fuel Oxygenates by a New Strain, Mycobacterium austroafricanum IFP 2012", Applied and Environmental Microbiology, Jun. 2002, pp. 2754-2762.
Francois et al., Applied and Environmental Microbiology, 2003.
V.I.Tishkov et al., "Catalytic Mechanism and Application of Formate Degydrogenase", Biochemistry, vol. 69, No. 11, Nov. 2004, pp. 1537-1554.
Joseph P Salanitro, "Understanding the Limitations of Microbial Metabolism of Ehters Used as Fuel Octane Enhancers", Current Opinion in Biotachnology, 1995, pp. 337-340.
Ken Williams et al., "Internal Protein Sequencing of SDS-Page-Separated Proteins: Optimization of an in Gel Digest Protocol", Techniques in Protein Chemistry VIII, 1997, pp. 79-90.
Rodney M. Hewick et al., "A gas-liquid solid phase peptide and protein sequenator", The Journal of Biological Chemistry, vol. 256, No. 15, Aug. 10, 1981, p. 7990-7997.
Technical Tips, INIST CNRS, Jan. 7, 1992.
Douglas Hanahan et al., "Plasmid Transformation of *Escherichia coli* and other Bacteria", Methods in Enzymology, vol. 204, 1991, pp. 63-113.
Jiong Ma et al., "Correlations between shine-dalgarno sequences and gene features such as predicted expression levels and operon structures", Journal of Bacteriology, Oct. 2002, pp. 5733-5745.
Mathieu Picardeau et al., "Analysis of the internal replication region of a mycobacterial linear plasmid", Microbiology, 2000, pp. 305-313.
Stephen F. Altschul et al., "Gapped blast and psi-blast: a new generation of protein database search programs", Nucleic Acids Research, vol. 25, No. 17, 1997, pp. 3389-3402.
Database EMBL, "Sequence 204 from Patent WO02052044", Oct. 5, 2002.
Database Geneseq, "Klebsiella pneumoniae polynucleotide seqid 5495", Jul. 29, 2004.
Database Geneseq, "NOV protein-related forward PCR primer SEQ ID 325", Dec. 18, 2003.
Database EMBL, "Oryza sativa (japonica cultivar-group) cDNA, partial sequence (S13004_4A)", Mar. 9, 1995.
Database Geneseq, "DNA analysis method PCR primer universal C beacon", May 4, 2001.
Database Geneseq, "Halohydrin dehydrogenase gene", Jun. 20, 2003.
Database Geneseq, "Primer of the invention #135", Oct. 21, 2004.
Database EMBL, "81490rsicen_8503.y1 *Oryza sativa* cv. LYP9 booting whole plant cDNA library *Oryza sativa* (indica cultivar-group) cDNA 5, mRNA sequence", Feb. 6, 2005.

(Continued)

*Primary Examiner*—Delia M Ramirez
*Assistant Examiner*—Md. Younus Meah
(74) *Attorney, Agent, or Firm*—Young & Thompson

(57) ABSTRACT

The invention concerns an isolated or purified polypeptide having an activity in the MTBE degradation path, and/or at least one of the catabolic intermediates of MTBE, preferably selected from the group consisting of tert-butyl alcohol (TBA), 2-methyl 1,2-propanediol (2-M1, 2-PD), hydroxy-isobutyraldehyde, hydroxyiso-butyric acid (HIBA), said polypeptide being selected from the group consisting of: a) a polypeptide comprising a sequence of amino acids selected from the group consisting of SEQ ID NO:2, SEQ ID NO:4, SEQ ID NO:6, SEQ ID NO:8 or SEQ ID NO:10; b) a polypeptide comprising a sequence of amino acids having at least 70% identity, preferably 75%, 80%, 90%, 95%, 98% or 99% with the sequence of amino acids of a polypeptide as defined in a); a polypeptide as defined in a) or b) whereof the sequence of amino acids comprises a substitution, deletion, insertion, addition or mutation of one or several amino acids over its entire length.

2 Claims, 15 Drawing Sheets

OTHER PUBLICATIONS

Figure 1:
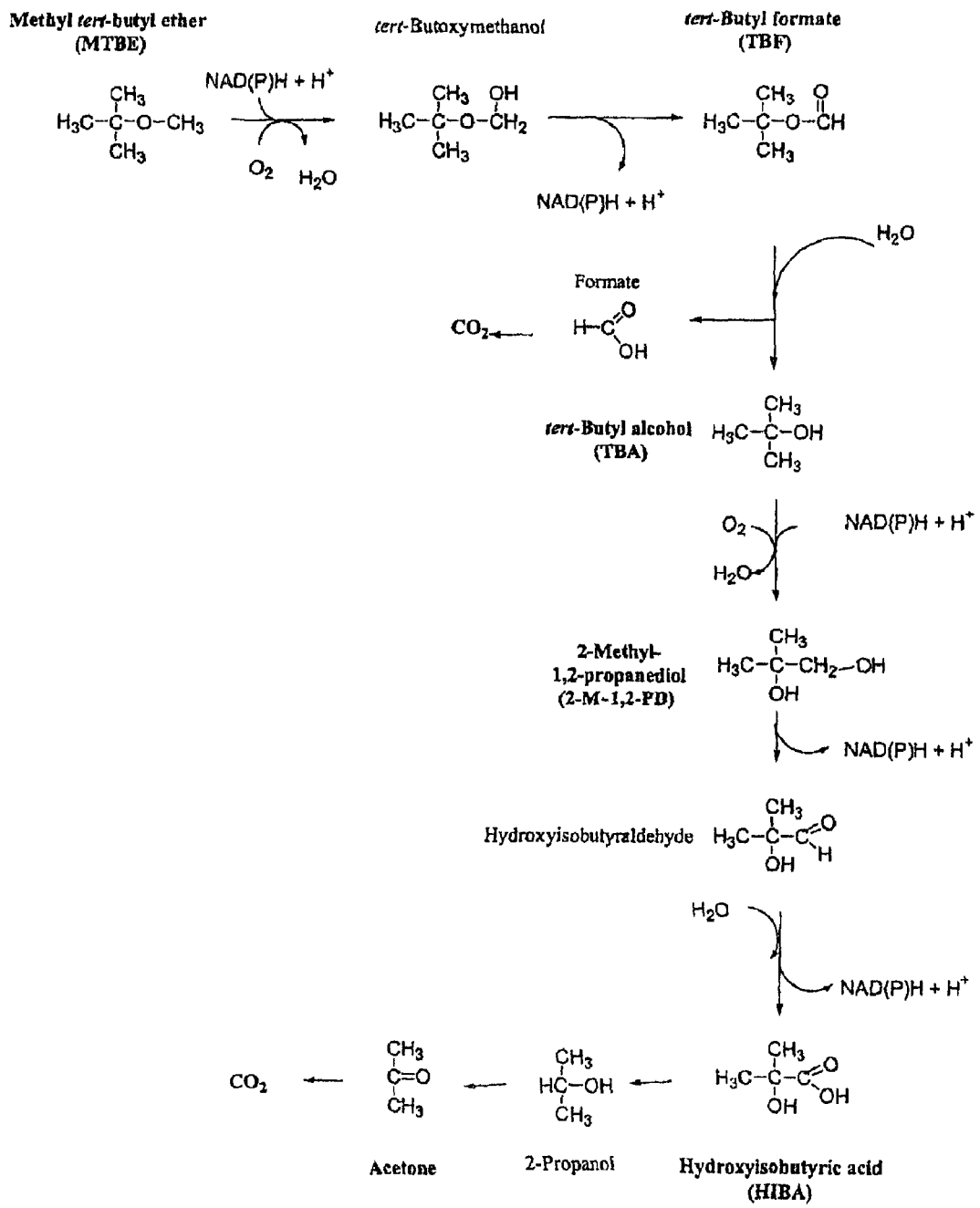

Database EMBL, "vz90h06.r1 Soars 2 NbMT Mus musculus cDNA clone Image:1344539 5' similar to TR:P97301 P97301 Stromal cell derived factor receptor 2;, mRNA sequence", Oct. 1, 1998.

Database Geneseq, "Human SNP oligonucleotide #7647", Jan. 24, 2002.

Database EMBL, "OsIRUA004936 *Oryza sativa* Express Library *Oryza sativa* (indica cultivar-group) genomic, genomic survey sequence", Sep. 22, 2004.

Database EMBL, "*Rhodococcus* sp. Ph12 cyclohexanone oxidation gene cluster, partial sequence", Jan. 13, 2003.

Fiorenza Stephanie et al., "Review of MTBE biodegradation and bioremediation", Bioremediation Journal, vol. 7, No. 1, Mar. 2003, pp. 1-30.

Francois A et al, "Comparison of MTBE and TAME degradation pathways in *Mycobacterium austroafricanum* IFP 2012", FEMS Congress of European Microbiologists Abstract Book, No. 1, 2003, p. 379.

Francois A et al., "Roles of tert-butyl formate, tert-butyl alcohol and acetone in the regulation of methyl tert-butyl ether degradation by *Mycobacterium austroafricanum* IFP 2012", Applied Microbiology and Biotechnology, vol. 62, No. 2-3, Aug. 2003, pp. 256-262.

Piveteau P. et al., "Biodegradation of tert-butyl alcohol and related xenobiotics by a methylotrophic bacterial isolate", Applied Microbiology and Biotechnology, vol. 55, No. 3, Apr. 2001, pp. 369-373.

Deeb Rula A et al., "Aerobic MTBE biodegradation: An examination of past studies, current challenges and future research directions", Biodegradation, vol. 11, No. 2-3, 2000, pp. 171-186.

Hristova K R et al., "Characterization of enzymes involved in MTBE biodegradation in *Aquiabacterium* sp. strain PM1", Abstracts of the General Meeting of the American Society for Microbiology, vol. 102, 2003, pp. Q-078.

Ju K et al., "Physiological characterization of MTBE metabolism by a new bacterial isolate", Abstracts of the General Meeting of the American Society for Microbiology, vol. 103, 2003, pp. Q-042.

Fayolle F et al., "Microbial degradation and fate in the environment of methyl tert-butyl ether and related fuel oxygenates", Applied Microbiology and Biotechnology 2001 Germany, vol. 56, No. 3-4, 2001 pp. 339-349.

Johnson E L et al., "Induction of methyl tertiary butyl ether (MTBE)-oxidizing activity in mycobacterium vaccae job5 by MTBE", Applied and Environmental Biotechnology 2004 U.S., vol. 70, No. 2, 2004, pp. 1023-1030.

Ferreira Nicolas Lopes et al., "Genes involved in the methyl tert-butyl ether (MTBE) metabolic pathway of *Mycobacterium austroafricanum* IFP 2012", Microbiology May 2006, vol. 152, No. Pt5, May 2006, pp. 1361-1374.

Ferreira Nicolas Lopes et al., "Isolation and characterization of a new *Mycobacterium austroafricanum* strain, IFP 2015, growing on MTBE", Applied Microbiology and Biotechnology 2006 Germany, vol. 70, No. 3, 2006, pp. 358-365.

\* cited by examiner

Cluster of *mpd* genes

BLAST analysis of SED ID NO :1

"NCBI Conserved Domain Search" analysis of SEQ ID NO :5

Hydropathy analysis of polypeptide SEQ ID NO : 8
by the software "Predict Protein".

POLYPEPTIDES HAVING AN ACTIVITY IN THE MTBE DEGRADATION PATH AND USES THEREOF

This is application is a 371 of PCT/FR06/01758, filed Jul. 18, 2006, which claims priority on foreign application France 0507577, filed Jul. 18, 2005.

The present application relates to the field of microbiology, more particularly to the use of microorganisms for treating wastewater contaminated with chemical pollutants, in particular methyl tert-butyl ether (MTBE) and/or catabolites of this compound.

The present invention relates to novel polypeptides and their fragments, and to the nucleic acids which code for these polypeptides and which are isolated from microorganisms capable of metabolizing MTBE and/or at least one of the catabolites of MTBE, preferably tert-butyl alcohol (TBA), 2-methyl-1,2-propanediol (2-M-1,2-PD), hydroxyisobutyraldehyde, hydroxyisobutyric acid (HIBA). The invention also relates to cloning and/or expression vectors comprising said nucleic acids, to bacterial cells transformed with said nucleic acids or said vectors, and their uses.

The invention also relates to a method of identifying microorganisms capable of metabolizing MTBE, and/or at least one of the catabolites of MTBE. More particularly, the present invention relates to a novel bacterial strain *Mycobacterium austroafricanum* deposited in the collection CNCM as number I-3401.

The invention also relates to a method of treating wastewater contaminated with MTBE and/or at least one of the catabolites of MTBE.

The chemical compound MTBE is used, as additive to lead-free petrols. Since the use of lead alkyls is forbidden owing to their toxicity, MTBE is added to the petrols in order to increase their octane number. The octane number measures the "knock resistance" of fuels when they combust as a mixture with air in the combustion chamber of engines. MTBE is also used as oxygen-containing compound which makes it possible to increase the oxygen content of petrols and thereby to improve their combustion efficacy. This makes it possible to reduce the release of uncombusted hydrocarbons and of carbon monoxide into the atmosphere. Thus, the MTBE concentrations which are currently used in oxygen-containing fuels amount to 15% (v/v). MTBE has been classified as a potential carcinogen by the US Environment Protection Agency (US E.P.A., December 1997 EPA/822/F-97/008. Office of Water, Washington, D.C., USA). The contamination of the environment with this compound may be due to inadequate storage of the petrol in non-tight tanks or to accidental spills. This type of waste may lead to serious environmental pollution problems such as contamination of subterranean aquifers. Consumers may be exposed to low concentrations when they drink non-drinking water from a source which is contaminated with MTBE. Moreover, the unpleasant taste and odor which MTBE imparts to the water, even at low concentrations, makes the latter unfit for consumption, which makes this xenobiotic compound an important pollutant. It appears that contamination with MTBE can largely be attributed to the fact that it is difficult to eliminate from the environment. MTBE proves to be persistent owing to its poor biodegradability and to the fact that it is readily soluble in water. The half-life of MTBE in aquifers is estimated to be at least 2 years (Wilson J. T., 2003, 19-61: In E. E. Moyer and P. T. Kostecki (ed.), *MTBE Remediation Handbook*. Amherst Scientific Publishers, Amherst, Mass.); in comparison, the value of benzene is 2 to 3 month under identical conditions. The contamination of aquifers may lead to serious hazards to public health. It is therefore necessary to develop efficient methods which allow the treatment of aquifers contaminated with MTBE or any other catabolite of MTBE.

Over the last few years, several studies on the determination of MTBE's biodegradability have been undertaken. A certain number of microorganisms capable of fully or partially assimilating MTBE have been identified and isolated. For example, certain microorganisms are capable of catabolizing MTBE by cometabolism. Two degradation pathways, both of which involve the initial oxidation of MTBE, lead to the production of tert-butyl alcohol (TBA) which, in most cases, accumulates in the medium. The bacterial strain *Mycobacterium vaccae* JOB5 is, when grown on propane, capable of oxidizing TBA, although this does not allow the production of compounds which it can utilize for its growth. Some strains of microorganisms which are capable of assimilating MTBE as carbon and energy source have been isolated (François et al., *Appl. Environ. Microbiol.*, 2002, 68: 2754-2762; Hanson, J. R. et al., *Appl. Environ. Microbiol.*, 1999, 65: 4788-4792; Hatzinger, P. B. et al., *Appl. Environ. Microbiol.*, 2001, 67: 5601-560). The enzymatic mechanisms of the initial attack of the MTBE in these bacteria remain to be elucidated.

The bacterial strain *Mycobacterium austroafricanum* I-2562 is one of the bacteria which are known for being capable of growing under aerobic conditions in the presence of MTBE. This strain is capable of catabolizing MTBE into a carbon and energy source (François et al., *Appl. Environ. Microbiol.*, 2002, 68: 2754-2762; U.S. Pat. No. 6,849,445). A certain number of degradation products or catabolites of MTBE have been identified, such as TBA, 2-M-1,2-PD, hydroxyisobutyraldehyde and HIBA. The degradation pathway of MTBE in this bacterial strain is shown in FIG. 1.

Figure 2:
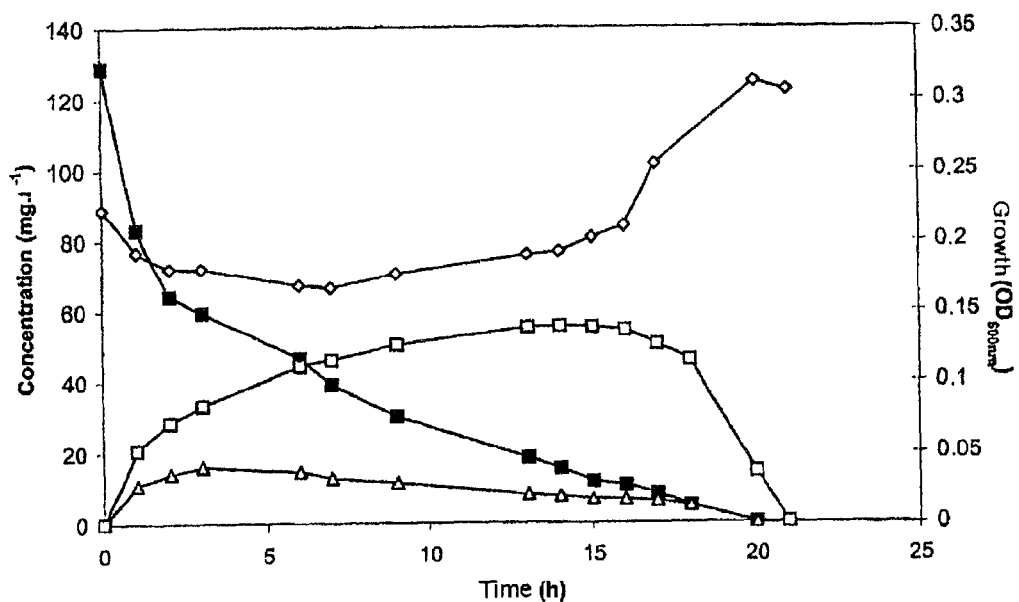

The kinetics of MTBE degradation, and the accompanying growth kinetics, in *M. austroafricanum* I-2562 show two clearly distinct phases (FIG. 2). The MTBE degradation kinetics are characterized by a very high degradation rate over the first 48 hours and which goes down from day 2 to day 16. During this period when MTBE is transformed into TBA, TBA accumulates, and no growth is observed. From day 16 to day 21, the accumulated TBA is broken down, which induces the microorganism's growth.

It should be noted that the first degradation step comprises the mineralization of the formate into $CO_2$, which requires the microorganism to be methylotrophic (François et al., *Appl. Environ. Microbiol.*, 2002, 68: 2754-2762). The $NAD(P)^+$-dependent formate dehydrogenase (or FDH) is an enzyme which plays an important role in the energy production of methylotrophic microorganisms. Moreover, this enzyme is frequently used in the regeneration of the $NAD(P)^+$-type cofactor in biocatalytic reactions (Tishkov, V. I. et al., *Biochemistry (Moscow)*, 2004, 69: 1537-1554). This first catabolic step does not generate ATP. François et al. have demonstrated that TBF has a negative effect on the MTBE degradation rate in *M. austroafricanum* I-2562 (François et al., *Appl. Microbiol. Biotechnol.* 2003, 62: 256-262). It has been suggested that the lack of reduced coenzyme equivalents and of energy are responsible for the slowing down of the enzymatic reactions (Salanitro, *Curr. Op. Biotechnol.*, 1995, 6: 337-340). It is highly likely that these are the main two reasons why the MTBE degradation rate slows down.

By allowing the net production of 2 NAD(P)H and of $2H^+$, the second step thus supplies the electron transport chain with $O_2$ as final electron acceptor during aerobiosis. Thus, it appears that this step is essential for the MTBE metabolism. The end result of this electron transport chain is the regeneration of $NAD(P)^+$ starting from NAD(P)H to reduce the $O_2$ to $H_2O$, whereby a proton transport gradient is created, the protons being used for the formation of ATP by the enzyme ATP synthase (proton pump). This corresponds to the oxidative phosphorylation mechanism and allows the synthesis of ATP, which is the energy compound of microorganisms (30.5 kJ product/mole ATP broken down due to a bond with high energy level).

One aim of the invention is to have available polypeptides capable of metabolizing MTBE and/or at least one of the MTBE catabolites, preferably TBA, 2-M-1,2-PD, hydroxyisobutyraldehyde, HIBA, and, if appropriate, to modify them and to use them for the treatment of wastewater contaminated with MTBE and/or at least one of the MTBE catabolites, preferably TBA, 2-M-1,2-PD, hydroxyisobutyraldehyde, HIBA.

The work by François et al. has demonstrated that several polypeptides were induced specifically in the presence of MTBE or TBA in *M. austroafricanum* IFP 2012 (I-2562). These specifically induced polypeptides were purified, digested with trypsin and then microsequenced. Analysis of the resulting sequences with the aid of the alignment tools Blast and Fasta has suggested that these polypeptides correspond to oxidoreductases which are implicated in the degradation of MTBE and TBA.

The applicant has carried out novel peptide sequencings on polypeptides which are specifically induced in the presence of MTBE, and a first probe of 204 base pairs has been obtained. This probe of 204 base pairs has, however, proven to be too short for a colony hybridization. Therefore, a large number of BLAST alignments were carried out with proteins with the greatest similarity to the amino acid sequence deduced from the 204 bp DNA fragment. After identification of amino acid sequences which are highly preserved in all these proteins, a large number of PCR amplifications have been carried out with degenerate primers, whereby a novel probe of 604 base pairs has been obtained. This probe of 604 base pairs has allowed the cloning of a DNA fragment comprising the mpdC gene, the orf1, the mpdB gene, the orf2 and a sequence corresponding to a putative transposase. Cloning this DNA fragment has proved to be difficult because after the first cloning, the clones obtained after transformation into *E. coli* were not stable, which made the extraction of the plasmid DNA difficult. After a large number of experiments, the applicant has put forward the hypothesis that the instability of the clones obtained was the result of the expression of the transposase gene, and has therefore cloned a DNA fragment in which the transposase gene is suppressed and which corresponds to the sequence SEQ ID No: 11. Thus, it was possible to obtain stable clones comprising the sequence SEQ ID No: 11.

The applicant has thus had to overcome a large number of cloning and sequencing difficulties in order to obtain the polypeptides according to the invention.

The present invention relates to any isolated or purified polypeptide with an activity in the degradation pathway of MTBE and/or at least one of the catabolites of MTBE, preferably TBA, 2-M-1,2-PD, hydroxyisobutyraldehyde, HIBA.

By specifying that the polypeptides or the nucleic acids coding for at least one inventive polypeptide are "isolated or purified", there is meant that they are placed into an environment which differs from the environment in which they are found naturally. They may be isolated or purified from a bacterial strain capable of growing in a medium comprising MTBE and/or at least one of the MTBE catabolites, preferably selected from the group consisting of TBA, 2-M-1,2-PD, hydroxyisobutyraldehyde, HIBA, among which in particular the *Mycobacterium austroafricanum* strains deposited in the CNCM collection as numbers I-3401 and I-2532. The molecules which have been modified by the present invention are also understood as being "isolated". It must be noted that the terms "isolated or purified" are also used for the host cells.

In the context of the invention, the terms "polypeptide, enzyme" and "protein" can be used interchangeably; they refer to molecules which are characterized by amino acid sequences of any length which are optionally modified chemically or biochemically. The term "polypeptide" also includes all of the mutated polypeptides which can exist naturally or variants, in particular in the bacterium of the *M. austroafricanum* strain, and which correspond to substitutions, deletions, insertions or additions of at least one amino acid. In the case of a substitution, one or more consecutive or nonconsecutive amino acids can be replaced by "equivalent" amino acids. Here, the expression "equivalent" amino acid refers to any amino acid which is capable of being substituted by one of the amino acids of the basic structure without, however, modifying the biological activity of the inventive polypeptides. These equivalent amino acids can be determined either on the basis of their structural homology with the amino acids which they substitute or on the basis of the results obtained in biological cross-activity tests which the different polypeptides may give.

In a preferred embodiment, the inventive polypeptide is selected from the group consisting of:

a) a polypeptide comprising an amino acid sequence selected from the group consisting of SEQ ID No: 2, SEQ ID No: 4, SEQ ID No: 6, SEQ ID No: 8 or SEQ ID No: 10, b) a polypeptide comprising an amino acid sequence with at least 70% identity, preferably 75%, 80%, 90%, 95%, 98% or 99% identity, with the amino acid sequence of a polypeptide as defined in a), c) a polypeptide as defined in a) or b) whose amino acid sequence comprises a substitution, deletion, insertion, addition or mutation of one or more amino acids over its entire length.

Different protocols which are known to the skilled worker have been described for introducing mutations in polypeptides. To modify the amino acid sequence of a polypeptide, one will typically act on the nucleic acid molecule which codes for this polypeptide. To modify the nucleic acid which codes for an inventive polypeptide, it is possible to treat it with a mutagenic agent, that is to say a physical or chemical agent capable of causing mutations which alter the meaning of the codons, which, as a result of the genetic code, modifies the amino acid sequence. It is advantageous to resort to a directed mutagenesis technique in order to modify the nucleotide sequence of a nucleic acid coding for at least one polypeptide of the gene and that of inventive polynucleotides; thus, one specifically introduces one or more mutations into the nucleic acid under consideration which, as a result of the genetic code, leads to the substitution of one or more amino acids by one or more other amino acids in the polypeptide encoded by the mutated polynucleotide. The reason why carrying out these mutations is of interest is not only the study of the biological activity of one of the inventive polypeptides in the degradation pathway of MTBE and/or at least one of the catalytic intermediates, but optionally the optimization of said activity of the polypeptide in recombinant form with a view to applying it industrially.

By "polypeptide fragment" there is meant a polypeptide comprising at least 15 consecutive amino acids, preferably 17, 20, 23, 25, 30, 40, 50, 100, 250 or 300 consecutive amino acids. The fragments of the inventive polypeptide which can be obtained by cleaving said polypeptide with a proteolytic enzyme, a chemical reagent or else by placing said polypeptide into a highly acidic environment are also part of the invention.

By "biologically active fragment" there is understood a fragment of amino acid sequences of an inventive polypeptide having at least one of the functional characteristics or properties of said polypeptide, in particular in as far as it has an activity in the degradation pathway of MTBE and/or at least one of the MTBE catabolites, preferably TBA, 2-M-1,2-PD, hydroxyisobutyraldehyde and HIBA.

Figure 3:
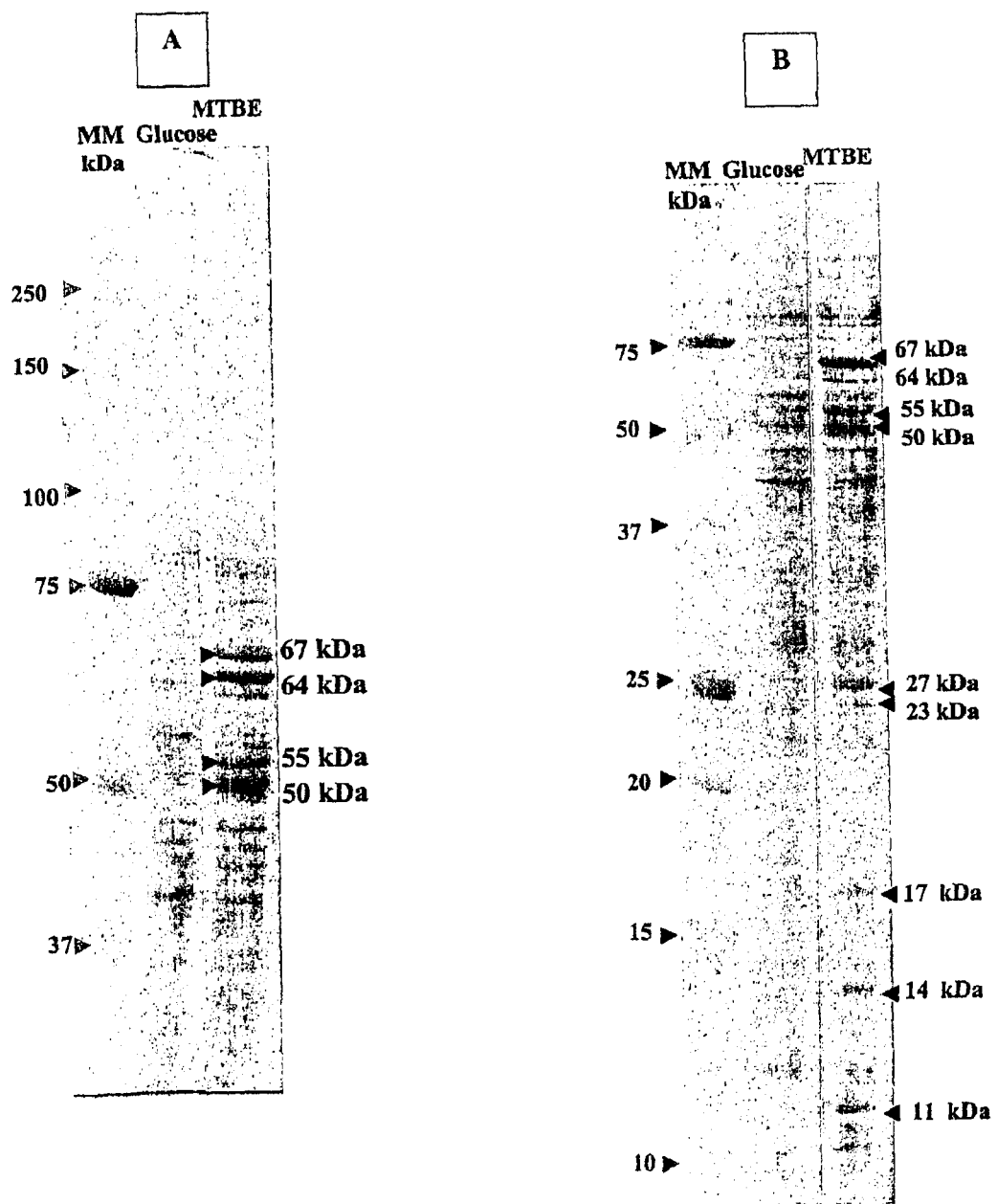

In accordance with a preferred embodiment, the expression of inventive polypeptides is induced when the bacteria which are capable of assimilating MTBE and/or at least one of the MTBE catabolites, among which in particular bacteria of the strain *M. austroafricanum*, more preferably the bacteria I-2562 or I-3401, are in a medium comprising MTBE and/or at least one of the MTBE catabolites, preferably TBA, 2-M-1,2-PD, hydroxyisobutyraldehyde and HIBA. Preferably, the polypeptides whose expression is induced at high level are the polypeptides SEQ ID No: 2, SEQ ID No: 4 and SEQ ID No: 6 as defined in a), b) or c) as shown in FIG. 3.

Advantageously, polypeptide SEQ ID No: 2 as defined in a), b) or c) with the name MpdC has an aldehyde dehydrogenase activity. In the catabolic pathway of MTBE, the inventive polypeptide MpdC is preferably capable of dehydrogenating hydroxyisobutyraldehyde to give HIBA.

Advantageously, polypeptide SEQ ID No: 6 as defined in a), b) or c) with the name MpdB has an alcohol dehydrogenase activity. In the catabolic pathway of MTBE, the inventive polypeptide MpdB is preferably capable of dehydrogenating 2-M-1,2-PD to give hydroxyisobutyraldehyde.

Advantageously, polypeptide SEQ ID No: 8 as defined in a), b) or c) has a permease activity, preferably a di/tripeptide permease activity. Said polypeptide preferably comprises 5 transmembrane segments.

Advantageously, polypeptide SEQ ID No: 10 as defined in a), b) or c) with the name MpdR has a transcriptional regulator activity.

The present invention also relates to any purified or isolated nucleic acid coding for at least one inventive polypeptide. Preferably, the present invention relates to any isolated or purified nucleic acid coding for at least one polypeptide with an activity in the degradation pathway of MTBE or at least one catabolite of MTBE, preferably TBA, 2-M-1,2-PD, hydroxyisobutyraldehyde and HIBA.

In the context of the invention, the terms "nucleic acid" and "DNA" are used interchangeably. By "nucleic acid" there is understood a precise array of modified or unmodified nucleotides which allows the definition of a fragment or a region of a nucleic acid, optionally which comprises non-natural nucleotides, and which may also be a double-stranded DNA, a single-stranded DNA or transcription products of said DNAs, and/or an RNA fragment.

In a preferred embodiment, the nucleic acid according to the invention, is selected from the group consisting of:

e) a nucleic acid comprising at least any one of the nucleotide sequences selected from the group consisting of SEQ ID No: 1, SEQ ID No: 3, SEQ ID No: 5, SEQ ID No: 7 or SEQ ID No: 9, or its complement, f) a nucleic acid comprising at least one nucleotide sequence with at least 70% identity, preferably 75%, 80%, 90%, 95%, 98% or 99% identity, with the nucleotide sequence of a nucleic acid as defined in e), g) a nucleic acid coding for at least one variant of a polypeptide comprising any one of the amino acid sequences SEQ ID No: 2, SEQ ID No: 4, SEQ ID No: 6, SEQ ID No: 8 or SEQ ID No: 10, where said nucleic acid hybridizes with the complement of a nucleic acid as defined in e) or f), h) a nucleic acid as defined in e), f) or g) whose sequence comprises a substitution, deletion, insertion, addition or mutation of one or more nucleotides over its entire length.

By "complement" there is understood any nucleic acid whose nucleotides are complementary to those of the sequence SEQ ID No: 1, SEQ ID No: 3, SEQ ID No: 5, SEQ ID No: 7 or SEQ ID No: 9 and whose orientation is reversed.

By "percentage identity" between two nucleic acid sequences or amino acid sequences there is understood, for the purposes of the present invention, a percentage of nucleotides or amino acids which are identical between the two sequences to be compared. The percentage identity between two nucleic acid sequences or amino acid sequences is determined by comparing these two sequences which are aligned in a meaningful manner, where the nucleic acid sequence or amino acid sequence to be compared may comprise additions or deletions in comparison with the reference sequence to produce a meaningful alignment between those two sequences. The percentage identity is calculated by determining the number of identical positions for which the nucleotide or amino acid is identical between the two sequences, dividing this number of identical positions by the total number of positions compared, and multiplying the result obtained by one hundred in order to arrive at the percentage identity between those two sequences. By "meaningful alignment" there is understood the alignment for which the percentage identity determined as hereinbelow is the highest. To obtain a meaningful alignment, preferably the BLAST program will be used.

In accordance with a preferred embodiment, the inventive nucleic acid comprises at least two of the nucleotide sequences selected from the group consisting of SEQ ID No: 1, SEQ ID No: 3, SEQ ID No: 5, SEQ ID No: 7 or SEQ ID No: 9 as defined in e), f), g) or h), preferably 3 of said nucleotide sequences, more preferably 4 of said nucleotide sequences, more preferably 5 of said nucleotide sequences.

The inventive nucleic acid advantageously comprises the nucleotide sequences SEQ ID No: 1 and SEQ ID No 5 as defined in e), f), g) or h), preferably SEQ ID No: 1, SEQ ID No: 3 and SEQ ID No: 5 as defined in e), f), g) or h).

The inventive nucleic acid advantageously comprises the nucleotide sequence SEQ ID No: 11.

In a preferred embodiment, the transcription of the inventive nucleic acid is under the control of a single promoter. By "promoter" there is meant a regulatory region located upstream of an open reading frame (ORF) near its 5' end. In the present application, the terms "ORF" and "gene" will be used interchangeably. A promoter comprises certain characteristic nucleotide sequences which allow the transcription initiation complex to be attached and transcriptional regulators to be attached.

In accordance with another preferred embodiment, the inventive nucleic acid is characterized in that its transcription is induced by the presence of MTBE and/or at least one of the catabolites of MTBE, preferably selected from the group consisting of TBA, 2-M-1,2-PD, hydroxyisobutyraldehyde, HIBA. Advantageously, the inventive nucleic acid is organized as an operon.

In a preferred, embodiment, the inventive nucleic acid is a cluster comprising nucleic acids coding for SEQ ID No: 1, SEQ ID No: 3, SEQ ID No: 5, SEQ ID No: 7 and SEQ ID No: 9, said cluster now being referred to as mpd cluster. The mpd cluster is shown diagrammatically in FIG. 7.

In accordance with a preferred embodiment, the inventive nucleic acid is a recombinant nucleic acid. By "recombinant nucleic acid" there is meant a single- or double-stranded nucleic acid molecule which has been modified by human intervention so as to contain fragments of nucleic acids which are combined or juxtaposed in the form of an arrangement which does not exist as a natural state.

The invention also relates to any expression and/or cloning vector comprising an inventive nucleic acid. By "vector" there is meant an extrachromosomal nucleic acid molecule, in particular a plasmid, which replicates autonomously and can be incorporated into a "host cell".

A cloning vector is typically designed so as to permit the transport of a cloned DNA fragment and contains one or more restriction enzyme recognition sites which allow the insertion or cloning of a nucleic acid fragment, as well as one or more nucleotide sequences which code for genes which allow the identification and selection of host cells which are transformed with said vector, such as genes for resistance to antibiotics.

In accordance with a preferred embodiment, the inventive expression vector is designed in such a way that it allows the expression of a coding nucleotide sequence which is inserted downstream of a promoter. The inserted sequence, or insert, will now be transcribed and then translated into a polypeptide. The inventive vector is advantageously flanked by elements which ensure the expression of at least one inventive nucleic acid in the host cell. Certain expression vectors advantageously have a tag coding sequence upstream or downstream of the insertion site or cloning site; the inserted nucleic acid will now be transcribed and then translated in the form of a fusion protein. By "fusion protein" there is meant a hybrid polypeptide comprising a polypeptide encoded by an inventive nucleic acid and a polypeptide capable of attaching itself to affinity matrices and/or of being recognized by antibodies which allow the detection and/or purification of the polypeptide to which it is fused.

In accordance with another preferred embodiment, the inventive vector comprises at least one sequence which is homologous to a nucleic acid sequence which is present in the genome of a host cell and which ensures its integration into said genome.

The invention furthermore relates to an isolated host cell comprising either at least one of the inventive nucleic acids and/or at least one of the inventive vectors. The following may be mentioned among the host cells which may be used for the purposes of the present invention: a prokaryotic cell, preferably a bacterial cell, more preferably a bacterial cell selected from the group consisting of *Mycobacterium smegmatis* mc2 155, *Escherichia Coli, Rhodococcus ruber* (deposited in the collection CNCM under the name *Gordonia terrae* and the number CIP I-1885).

The inventive polypeptides can be prepared and/or obtained by any technique with which the skilled worker is familiar. In particular, they may be obtained by chemical synthesis, but also by molecular-biology techniques, using in particular PCR, expression vectors and suitable host cells such as described hereinabove. The inventive polypeptides are preferably characterized in that it is possible by their expression in host cells, in particular bacterial host cells, to satisfy the requirements of degradation of MTBE and/or at least one of the catabolites and allow the growth of said bacteria.

The present invention also relates to an oligonucleotide primer comprising a fragment of at least 15 consecutive nucleotides, preferably a fragment of 15, 17, 20, 23, 25, 27, 30, 35, 40, 45 or 50 consecutive nucleotides, of the nucleotide sequence selected from the group consisting of SEQ ID No: 1, SEQ ID No: 3, SEQ ID No: 5, SEQ ID No: 7 or SEQ ID No: 9, or having a sequence with at least 70% identity, preferably 75%, 80%, 90%, 95%, 98% or 99% identity, with the nucleic acid sequence of said fragment.

The present invention also relates to an oligonucleotide primer comprising a fragment of at least 15 consecutive nucleotides, preferably a fragment of 15, 17, 20, 23, 25, 27, 30, 35, 40, 45 or 50 consecutive nucleotides, of the nucleotide sequence SEQ ID No: 12, or having a sequence with at least 70% identity, preferably 75%, 80%, 90%, 95%, 98% or 99% identity, with the nucleic acid sequence of said fragment. The sequence SEQ ID No: 12 corresponds to the nucleotide sequence of the 16S rDNA of strain *M. austroafricanum* I-2532.

The present invention relates to a probe comprising the nucleotide sequence which is complementary to a fragment of at least 15 consecutive nucleotides, preferably a fragment of 15, 17, 20, 23, 25, 27, 30, 35, 40, 45 or 50 consecutive nucleotides, of the nucleotide sequences selected from the group consisting of SEQ ID No: 1, SEQ ID No: 3, SEQ ID No: 5, SEQ ID No: 7 or SEQ ID No: 9, or having a sequence with at least 70% identity, preferably 75%, 80%, 90%, 95%, 98% or 99% identity, with the nucleic acid sequence of said fragment.

The present invention also relates to a probe comprising the nucleotide sequence which is complementary to a fragment of at least 15 consecutive nucleotides, preferably a fragment of 15, 17, 20, 23, 25, 27, 30, 35, 40, 45 or 50 consecutive nucleotides, of the nucleotide sequence SEQ ID No: 12, or having a sequence with at least 70% identity, preferably 75%, 80%, 90%, 95%, 98% or 99% identity, with the nucleic acid sequence of said fragment.

By "probe" there is understood a nucleic acid fragment which is labeled by incorporation of radioactive atoms or of fluorescent groups and whose sequence has substantial complementarity with the sought nucleic acid sequence; the latter will be detected by hybridization with the probe, and this hybridization is produced when the two complementary sequences pair. By "complementary sequence" there is meant a nucleotide sequence which is composed of a succession of bases which are complementary to the succession of another sequence with which it can thus hybridize. The hybridization of a probe with a size of above 200 nucleotides is preferably carried out at a temperature of approximately 60° C. following a modification of what has been described by Sambrook et al. (*Molecular Cloning: A Laboratory Manual*. Cold Harbor Laboratory Press, Cold Spring Harbor, N.Y., 2001).

More particularly, the present invention relates to a probe comprising a fragment of the mpdB gene of 591 base pairs whose sequence is the sequence SEQ ID No: 14 or a sequence with at least 70% identity, preferably 75%, 80%, 90%, 95%, 98% or 99% identity, with the nucleic acid sequence of said fragment.

The present invention also relates to a method of identifying a cell or a nucleic acid of a cell capable of degrading MTBE and/or at least one of the catabolites of MTBE, preferably selected from the group consisting of TBA, 2-M-1,2-PD, hydroxyisobutyraldehyde, HIBA, which comprises:
  optionally a step of seeding the cell on medium which is supplemented with MTBE and/or at least one of the catabolites of MTBE, preferably selected from the group consisting of TBA, 2-M-1,2-PD, hydroxyisobutyraldehyde, HIBA,
  a step in which the nucleic acids of said cell are screened by hybridization with at least one inventive probe, and/or
  a step in which at least one nucleic acid of said cell is amplified or polymerized with at least two inventive oligonucleotide primers.

In accordance with a preferred embodiment, a cell of a novel, strain capable of degrading MTBE and/or at least one of the catabolites of MTBE will be identified with the aid of oligonucleotide primers with which the 16S rRNA of said cell can be amplified.

Figure 12:
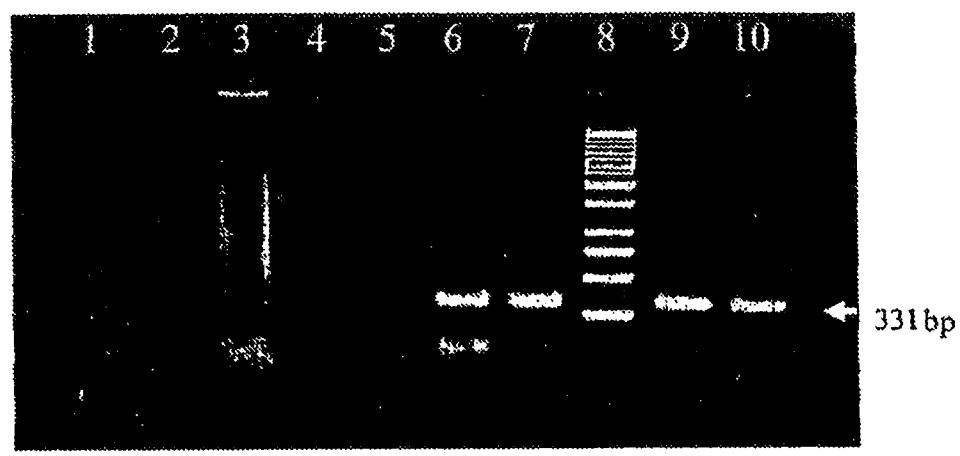

Advantageously, a primer pair (5'-TGCACACAGGCCA-CAACCCA-3') (SEQ ID NO: 15) and (5'-GAGAGTTTGATCCTGGCTCAG-3') (SEQ ID NO: 16) has been designed using two variable regions of the nucleotide sequence of the 16S rDNA of the *M. austroafricanum* strain. This primer pair is specific of the species *M. austroafricanum* in as far as it does not allow the 16S rDNA of microorganisms of other species, among which in particular the species *Nocardiacae*, which are incapable of assimilating MTBE and/or at least one of the catabolites of MTBE, to be amplified (FIG. 12).

Figure 10:
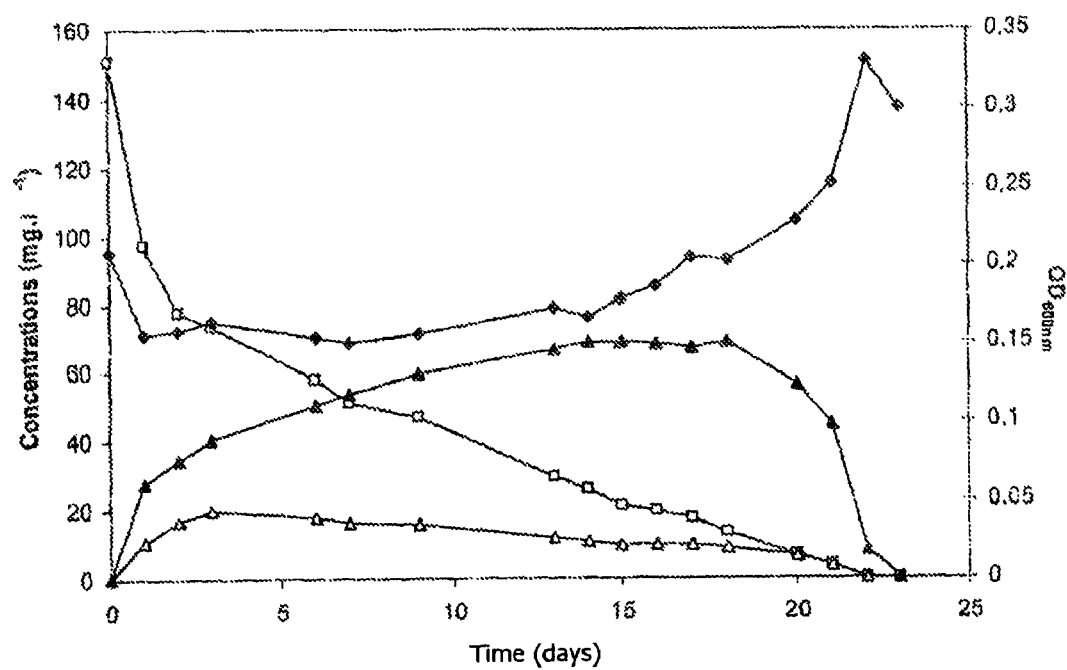

By carrying out the inventive method, a novel bacterial strain of *M. austroafricanum* has been identified; it is deposited in the collection CNCM as number I-3401. It has been isolated from surface water taken from the bottom of a storage tank of an MTBE-supplemented petrol. The growth of *M. austroafricanum* I-3401 on MTBE follows a degradation pathway which is similar to that of *M. austroafricanum* I-2562 (FIG. 10). Preferably, the novel strain *M. austroafricanum* I-3401 is characterized by the fact that it is capable of assimilating MTBE and/or at least one of the catabolites of MTBE, preferably selected from the group consisting of TBA, 2-M-1,2-PD, hydroxyisobutyraldehyde and HIBA. More preferably, the novel strain I-3401 is characterized by a nucleic acid sequence of the 16S rDNA which comprises the sequence SEQ ID No: 13.

The independent isolation of two strains of *M. austroafricanum*, I-2562 and I-3401, both of which are capable of growing on MTBE and which have been isolated from two distinct and distant geographical origins (activated sludges from a purification unit of a municipal wastewater plant of the Paris region, and surface water taken from the bottom of a storage tank of an MTBE-supplemented petrol located in the Southwest of France) demonstrates that such microorganisms, which are frequently isolated from soil and water samples (Jones and Jenkins, *Can. J. Microbiol.*, 1965, 11: 127-133; Viallier and Viallier, *Ann. Soc. Belge Med. Trop.*, 1973, 53: 361-371), can play an important role in the degradation of MTBE in contaminated aquifers.

The invention also relates to a kit for the detection and/or quantification of bacteria, preferably of bacteria of the strain *M. austroafricanum* on sites contaminated with MTBE and/or at least one of the catabolites of MTBE, preferably selected from the group consisting of TBA, 2-M-1,2-PD, hydroxyisobutyraldehyde and HIBA, said kit comprising at least one inventive probe and/or at least two inventive primers, which can be used separately or in combination, for example in DNA chips ("microarrays").

More particularly, the present invention relates to a DNA chip comprising a probe whose sequence is the sequence SEQ ID No: 14 or a sequence with at least 70% identity, preferably 75%, 80%, 90%, 95%, 98% or 99% identity, with the sequence SEQ ID No: 14.

The present invention also relates to the use of the polypeptide SEQ ID No: 2 as defined in a), b) or c) as aldehyde dehydrogenase, preferably for the dehydrogenation of hydroxyisobutyraldehyde to HIBA.

The present invention also relates to the use of the polypeptide SEQ ID No: 6 as defined in a), b) or c) as alcohol dehydrogenase, preferably for the dehydrogenation of 2-M-1,2-PD to hydroxyisobutyraldehyde.

Finally, the present invention relates to a method of treating aqueous effluents comprising MTBE, ETBE and/or at least one of the catabolites of MTBE, preferably selected from the group consisting of TBA, 2-M-1,2-PD, hydroxyisobutyraldehyde, HIBA, in order to reduce their concentration, comprising the seeding of said aqueous effluent with at least one inventive cell or identified by the inventive identification method. Advantageously, the inventive method is characterized in that the cell is bound to a suitable support, preferably a mineral support, more preferably a support comprising at least 50% by weight of partite.

The method according to the invention is particularly suitable for the treatment of an aquifer or a soil which is contaminated with MTBE and/or at least one of the metabolites of MTBE.

LIST OF FIGURES

FIG. 1. Metabolic pathway of the degradation of MTBE by *M. austroafricanum* I-2562.

The degradation intermediates which have been identified during our experiments are shown in bold.

FIG. 2. Growth of *M. austroafricanum* I-2562 on MTBE. During the growth, the $OD_{600\ nm}$ (◇-◇) and the MTBE (■-■), TBF (Δ-Δ) and TBA (□-□) concentrations have been measured.

FIG. 3. Electrophoresis on 10% polyacrylamide gels (A) or 15% polyacrylamide gels (B) in the presence of SDS (SDS-PAGE) of cell extracts from *M. austroafricanum* I-2562 obtained after growth on glucose or on MTBE. The molecular weights (in kDa) are shown on the right of the Figure.

Figure 4:
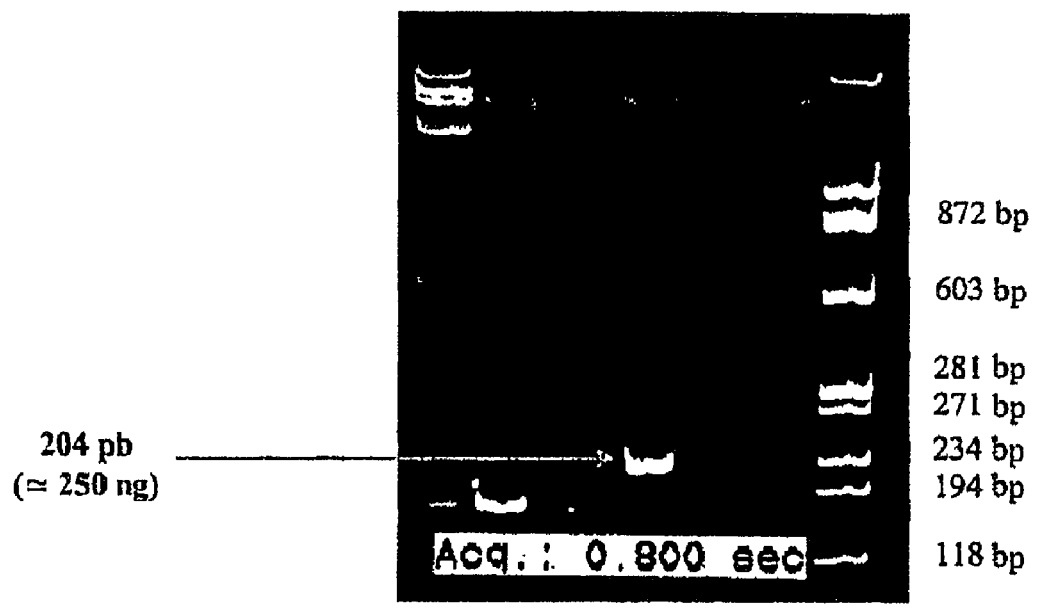

FIG. 4. PCR amplification of genomic DNA of *M. austroafricanum* I-2562 with the degenerate primers created using internal peptide sequences of the 64 kDa polypeptide induced on MTBE.

Figure 5:
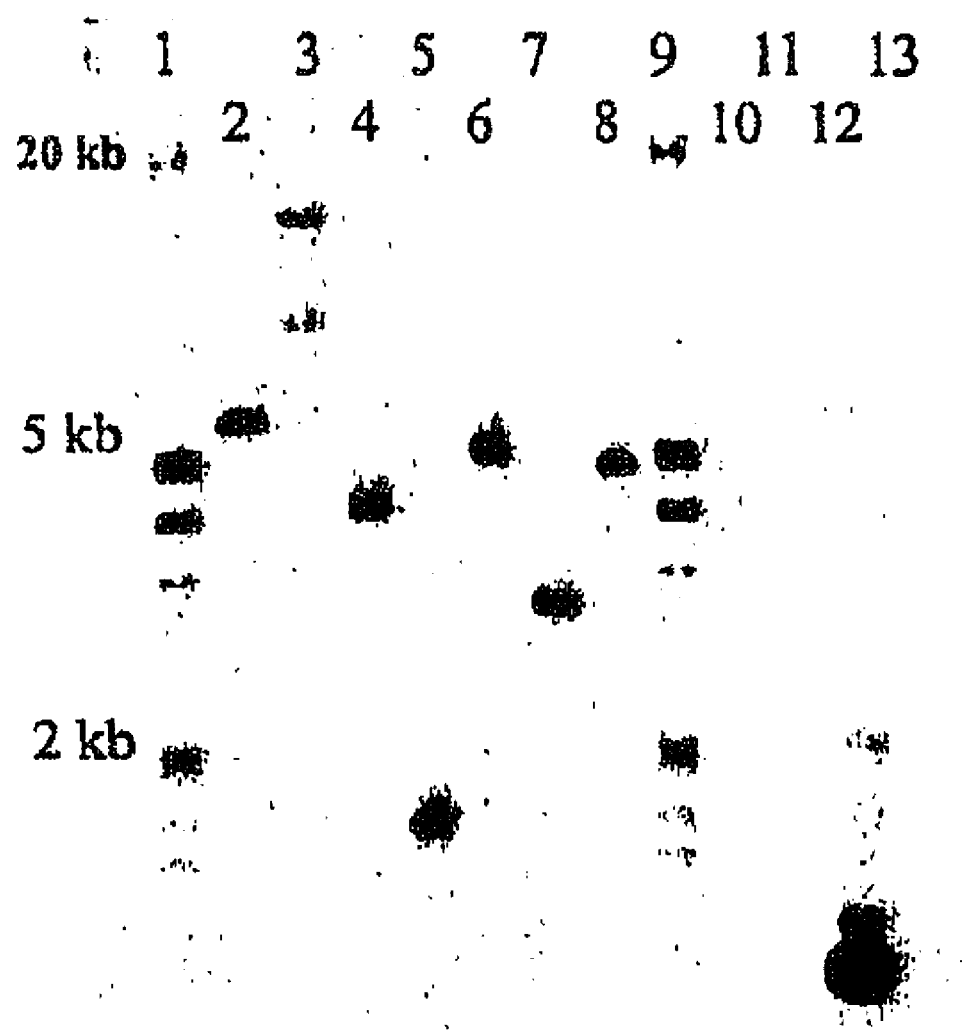

FIG. 5. Southern blot hybridization of genomic DNA of *M. austroafricanum* I-2562 after digestion using the 204 bp probe. The size of the bands developed is shown in kb. 5 μg genomic DNA of *M. austroafricanum* I-2562 are digested with the restriction enzymes BamHI, EcoRI, FspI, KnpI, NheI, Nru, PstI, Pvu II or SmaI (wells 2-8, respectively) and 50 ng of the 204 bp probe (well 12) are analyzed by Southern blot using the 204 bp probe. The positions which correspond to the migration of the DNA of the digoxigenin-labeled molecular weight marker III (Roche; well 1 and well 9) are shown on the left of the luminograph.

Figure 6:

FIG. 6. "Colony hybridization" of recombinant clones of *E. coli* DH10B with a 604 bp probe.

A) Luminography of membranes comprising the first clones which are the result of the digestion of *M. austroafricanum* I-2562 with SmaI. The positive clones (black spots) are detected with the digoxigenin-labeled mpdC probe.

B) Luminography of membranes comprising the first clones which are the result of the digestion of *M. austroafricanum* I-2562 with PstI. The positive clones (black spots) are detected with the digoxigenin-labeled mpdB probe.

Figure 7:
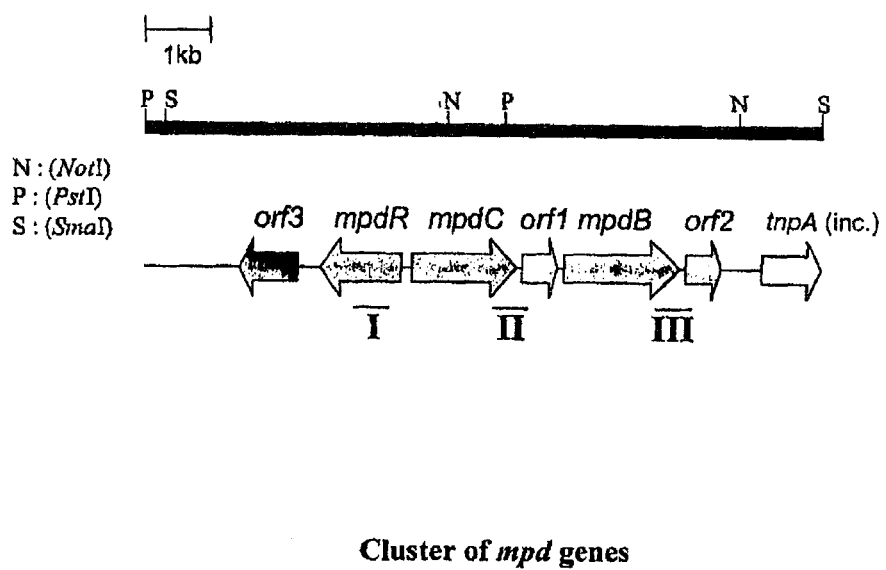

FIG. 7. Organization of the cluster of genes implicated in the MTBE degradation pathway and isolated from, genomic DNA of *M. austroafricanum* I-2562 (A), and their corresponding restriction map (B).

The ORF mpdR codes for a transcriptional regulator, and the ORF mpdC and mpdB code for an aldehyde dehydrogenase enzyme and an alcohol dehydrogenase enzyme, respectively. Three polypeptides of 64, 55 and 27 kDa are all expressed, at high level after growth of *M. austroafricanum* I-2562 on MTBE. The 25 kDa polypeptide is a permease. The PCR fragments obtained from the amplifications carried out with the aid of the primer pairs RT-PCR-F1/-R1, RT-PCR-F2/-R2 and RT-PCR-F3/-R3 are shown diagrammatically in FIG. 7 (fragments numbered I, II and III).

Figure 8:
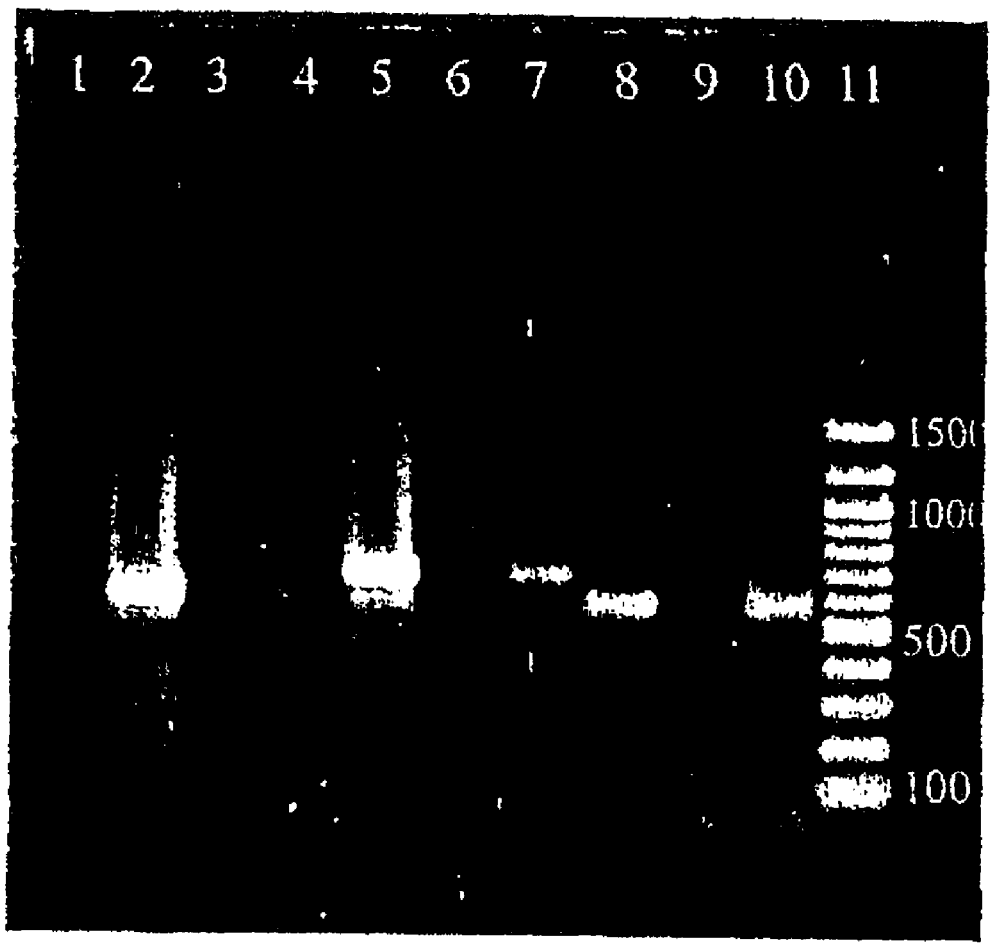

FIG. 8. RT-PCR of *M. austroafricanum* I-2562 after growth on TBA using the primers corresponding to the mpd cluster.

The primers used are mentioned in the table hereinbelow.

Key: Well 1: C⁻ PCR I, well 2: C⁺ PCR I, well 3: (−) RT-PCR I, well 4: (+) RT-PCR I, well 5: C⁺ PCR II, well 6: (−) RT-PCR II, well 7: (+) RT-PCR II, well 8: C⁺ PCR III, well 9: (−) RT-PCR III, well 10: (+) RT-PCR III, well 11: DNA marker (100 bp).

Figure 9:
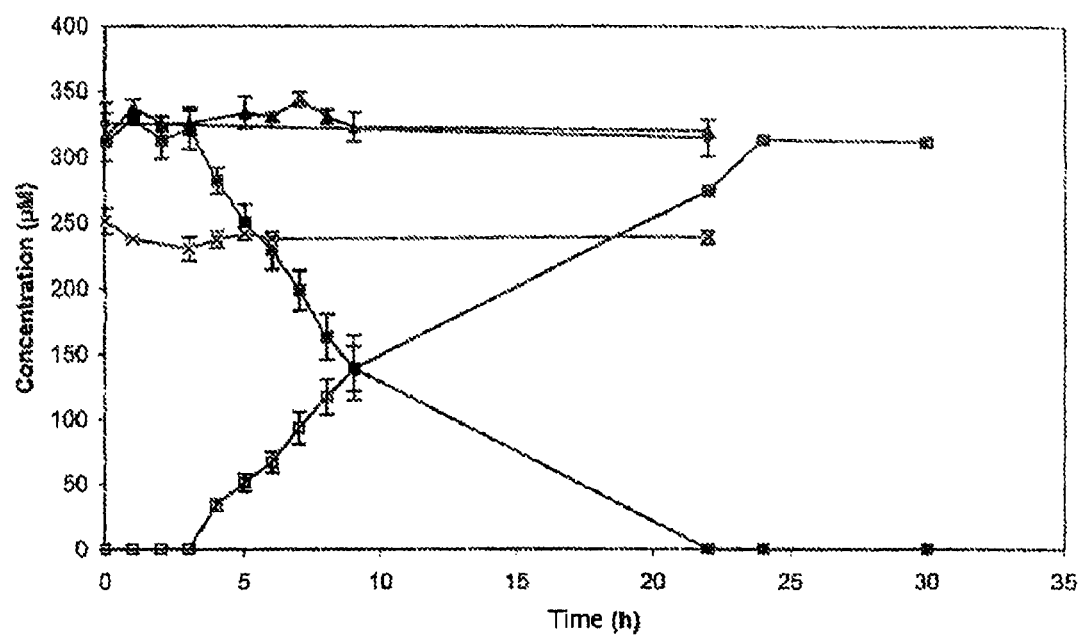

FIG. 9. Kinetics of the degradation of 2-M-1,2-PD by *M. smegmatis* mc2 155-clone 9 cells (squares) and of *M. smegmatis* mc2 155-pCL4D cells (triangles).

Degradation of 2-M-1,2-PD (filled symbols) and HIBA production (open symbols). Abiotic control (◊ - ◊). Cells of *M. smegmatis* mc2 155-clone 9 in the presence of 400 mg·L$^{-1}$ chloramphenicol (x-x).

The cell concentrations of *M. smegmatis* mc2 155-clone 9 and of *M. smegmatis* mc2 155-pCL4D were 233.33±14.09 and 214.63±21.95 mg·L$^{-1}$, respectively.

FIG. 10. Growth of *M. austroafricanum* I-3401 on MTBE. During the growth, the OD$_{600\ nm}$ (♦-♦) and the residual MTBE (□-□), TBF (Δ-Δ) and TBA (▲-▲) concentrations were measured.

Figure 11:
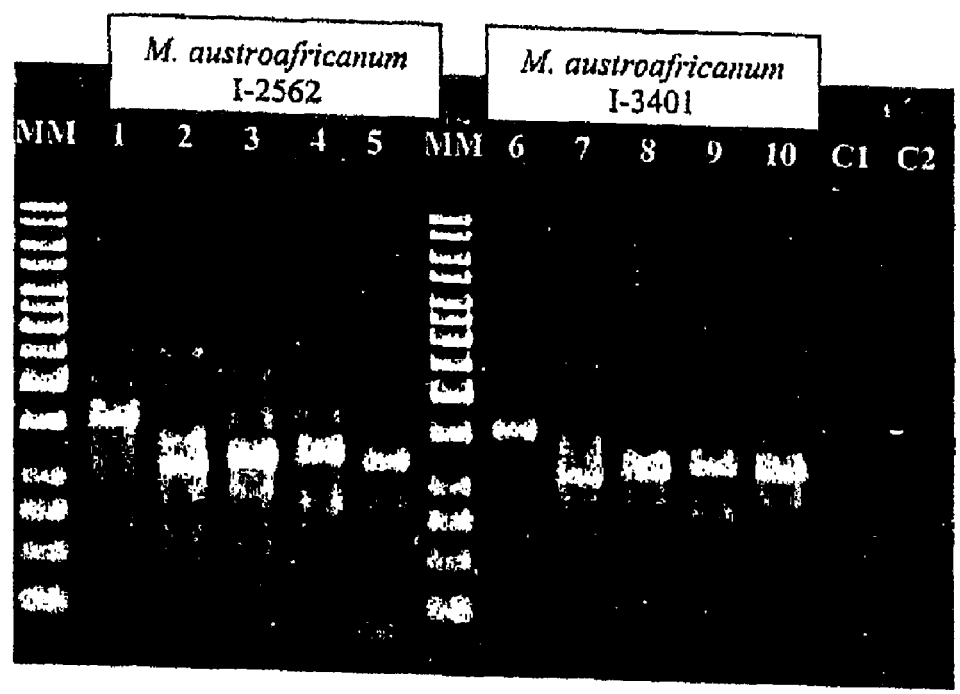

FIG. 11. PCR amplification of the mpd cluster in the genomic DNA of *M. austroafricanum* I-3401.

Key:

MM: 1 kb DNA marker,

Wells 1 and 6: amplification of the SEQ ID No: 9 coding for the 47 kDa polypeptide.

Wells 2 and 7: amplification of the SEQ ID No: 1 coding for the 55 kDa aldehyde dehydrogenase.

Wells 3 and 8: amplification of the SEQ ID No: 3 coding for the 27 kDa protein.

Wells 4 and 9: amplification of the SEQ ID No: 5 coding for the 64 kDa alcohol dehydrogenase.

Wells 5 and 10: amplification of the SEQ ID No: 7 coding for the 25 kDa protein, the putative permease.

C1 and C2: negative controls without primers of genomic DNAs of *M. austroafricanum* I-2562 and I-3401, respectively.

FIG. 12. Amplification of specific sequences of the 16S rDNA in various microorganisms.

The expected size of the PCR product is 331 bp.

The genomic DNAs of strains of *Rhodococcus ruber* (well 1), *Rhodococcus* sp. B-1 (well 2), *Pseudomonas resinovorans* CA10 (well 3), *Mycobacterium smegmatis* mc2 155 (well 4), *Escherichia coli* DH10B (well 5), *Mycobacterium austroafricanum* I-2562 (well 6), *Mycobacterium austroafricanum* I-3401 (well 7) and of samples originating from the middle of cassette 1 (well 9) and the middle of cassette 2 (well 10) of a pilot biobarrier seeded with *M. austroafricanum* I-2562 for the degradation of MTBE were used for carrying out PCR amplification reactions. GeneRuler™ 1 kb DNA Ladder was used as DNA molecular weight marker (well 8).

Figure 13:
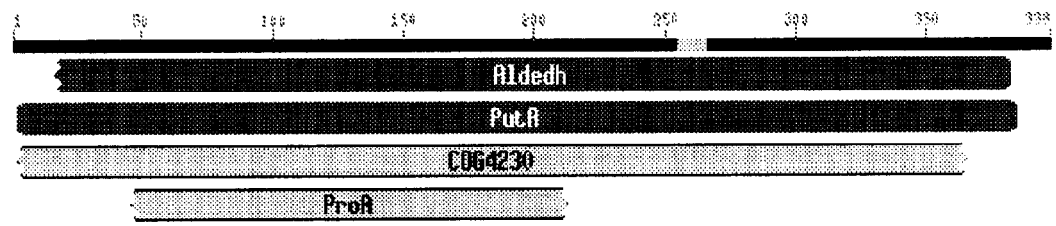

FIG. 13. BLAST analysis of SEQ ID NO:1.

Figure 14:
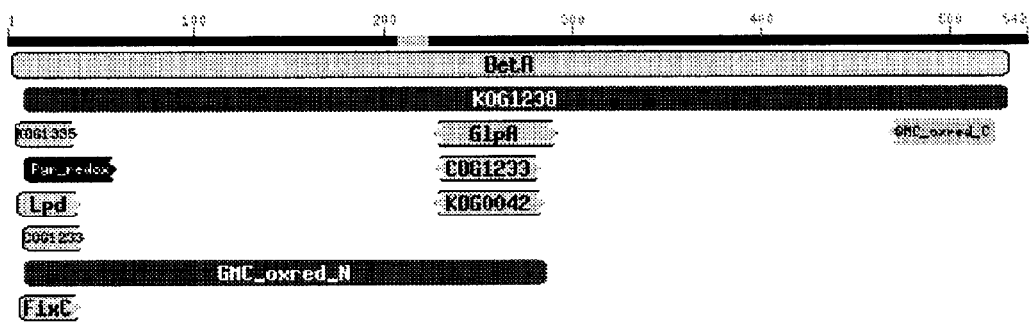

FIG. 14. "NCBI Conserved Domain Search" analysis of SEQ ID NO:5 detecting similarities with the protein encoded by BetA gene, which is a choline dehydrogenase.

Figure 15:
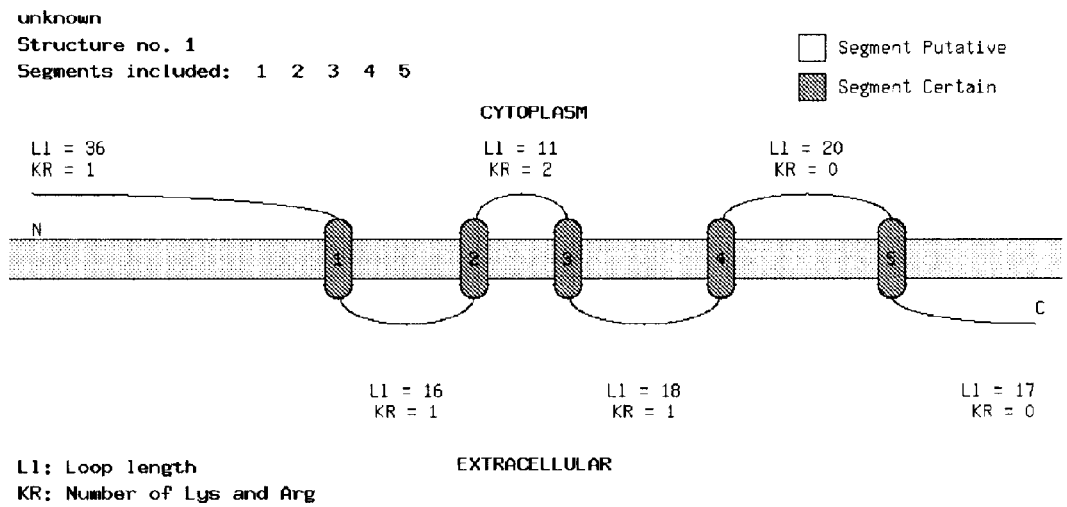

FIG. 15. Hydropathy analysis of polypeptide SEQ ID NO: 8 by the software "Predict Protein" reveals the presence of 5 transmembrane segments.

The present invention will be understood better with the aid of the examples which follow; these examples are merely illustrative, and are not understood as limiting the invention in any way.

EXAMPLE 1

Identification of Polypeptides Induced after Growth of Strain *M. austroafricanum* I-2562 on MTBE Cytoplasmic proteins were extracted from the culture on MTBE or on glucose in order to identify and to detect the presence of proteins induced specifically after growth of *M. austroafricanum* bacteria on medium comprising MTBE (FIG. 2).

1.1. Preparation of Protein Extracts

Cells of strain *M. austroafricanum* I-2562 are grown on 300 mL of the above-described (Piveteau et al., *Appl. Microbiol. Biotechnol.* 2001, 55: 369-373) defined mineral medium (MM) in the presence of MTBE or glucose as carbon source. The cultures are incubated aerobically at 30° C. in conical test tubes, with shaking. Growth is evaluated by measuring the absorbance (OD$_{600\ nm}$) on a UV-1601 spectrophotometer (Shimadzu Corporation, Kyoto, Japan). When the OD$_{600}$ is 1, the cells are collected by centrifugation at 20000×g for 15 min, washed twice with phosphate buffer (20 mM, pH 7) and resuspended in 5 mL of 50 mM Tris-HCl buffer (pH=8.0) comprising 0.1M dithiothreitol (DTT). The cells are disrupted by three passages through the French press (20000 psi), while always being maintained on ice. The cell debris is eliminated by two centrifugations at 1000×g for 2 min. The supernatant is used for analyzing the protein profile. The total protein concentration is measured using the Bio-Rad kit (Dye reagent, Bio-Rad laboratories GmbH, Munich, Germany).

1.2. Analysis of the Soluble Proteins

The electrophoresis of these extracts is carried out on SDS-PAGE gels with 10 or 15% polyacrylamide comprising SDS, following the method developed by Laemmli, except for the migration conditions (V=150 volts during the first hour followed by a constant A=33 mA during the following hours of migration). 12.5 µg of total protein are placed on the gel into each well, for each carbon source which is tested (Laemmli, *Nature*, 1970, 227: 680-685).

The protein profiles of high and low molecular weights which have developed on 10 or 15% acrylamide SDS-PAGE gels, respectively, have made it possible to detect 9 proteins of different molecular weights which were specifically induced by the presence of MTBE, (FIG. 3).

1.3. Identification of Two Peptide Sequences of the Polypeptide MpdC (64 kDa) which was Induced During the Growth on MTBE Internal Sequencing Protocol:

Each gel band which corresponds to a polypeptide which was induced specifically in the protein profile after *M. austroafricanum* I-2562 was grown on MTBE is excised and subsequently reduced with DTT "in the gel" and then the disulfide bridges are alkylated with iodoacetamide (Jenö et al., *Analytical Biochemistry*, 1995, 224: 75-82), followed by digestion with trypsin. The enzyme used, is the "sequencing grade" trypsin from Promega (Helman et al., 1995, William et al., *In: Techniques VIII*, Marshak, D., ed. Academic Press, San Diego, 1997, 79-90). The peptides thus generated are extracted from the remaining gel pieces by 3 treatments of 30 min at 60° C., each in the presence of 100 µL 1% TFA and 60% acetonitrile, followed by sonication for 10 min. A last extraction is carried out with 50 µL of pure acetonitrile over 10 min. The 4 extracts are mixed, and the liquid volume is reduced in a rotary evaporator (Savant AES1010) to obtain an end volume of 5 µL.

The peptides are now separated by HPLC (Vydac) on a C18 microbore column (300° A; 1×50 mm No. 218TP5105), using the Applied Biosystems 130A separation system. The peptides are eluted at 100 µL/min using a mixture of solvents A and B, with a gradient of the solvent mixture programmed thus: 3-63 min (0-50% B), 63-72 min (50-100% B) and 72-75 min (100% B). Solvent A is composed of 0.1% TFA in water, and solvent B is composed of 0.08% TFA in 70% acetonitrile and water, and the peptides are detected by a UV detector at 220 nm. The different fractions are collected manually in 1.5-mL-tubes and applied to glass fiber disks which have been pretreated by addition of 7 µL Biobrene (Applied Biosystems Inc.). The disks are subjected to Edman degradation on a Procise sequencer (model 494 cLC) following the protocol described by Hewick et al. (*J. Biol. Chem.*, 1981, 256: 7990-7997).

A quantity of peptide which is equivalent to approximately 1 pmol is applied to the sequencer, and a standard program using TFA as the liquid phase is used for the sequencing. The phenylthiohydantoin amino acid derivatives (PTH-aa) are determined by comparison with standards (PTH-standards, ABI) and analyzed on-line with the aid of a capillary separation system (ABI 140D) from the start-up of the sequencing.

Results:

Among the proteins identified, a protein which migrates at 64 kDa (named MpdC) is the protein with the highest induction level. The extraction from the corresponding gel band, and digestion with trypsin followed by micro-sequencing of internal peptides, have made it possible to obtain 2 sequences of this polypeptide.

The comparison with the aid of the BLAST software of the first internal sequence (KQRGWAYDPNVRGLPE) (SEQ ID NO: 36) has not shown significant similarities. In contrast, the BLAST analysis of the second internal sequence (STEHGLEGTIDWPISYEELAPYYDENDAIY) (SEQ ID NO: 37) shows a high degree of similarity (93%) with a large number of oxidases and dehydrogenases which belong to the GMC oxidoreductase family (Cavener, *J. Mol. Biol.*, 1992, 223: 811-814).

EXAMPLE 2

Preparation of Probes 2.1. Extraction of Genomic DNA

The genomic DNA was isolated from different strains tested in accordance with the protocol of Pospiech and Neumann which was modified in the following manner: a culture with 50 ml, of LB medium ($OD_{600\ nm}$ 0.7) is harvested by centrifugation for 15 min at 10000 g and 4° C. (Pospiech and Neumann, *Trends In Genetics*, 1995, 11: 217-218). The pellet is resuspended in 5 ml of SET buffer (75 mM NaCl, 25 mM EDTA, 20 mM Tris-HCl, pH 8). Lysozyme is added to a final concentration of 1 mg·mL$^{-1}$ and lysostaphin at 112 U·µL$^{-1}$ (Sigma). This reaction mixture is incubated for 1 h at 37° C.

After treatment with the mixture SDS/proteinase K, an extraction step is carried out in the following reaction mixture, where the different reactants are added in succession: ¼ volume of 5M NaCl, followed by ⅕ volume of 10% CTAB-0.7M NaCl (preheated to 65° C.), and the mixture is incubated for 1 h at 65° C. Thereafter, one volume of chloroform ($CHCl_3$) is added, and the following steps are carried out in accordance with the original protocol.

2.2 Preparation of a 204 bp Probe

The two peptide sequences obtained in example 1 were used to generate several degenerate primer pairs in accordance with the universal genetic code, taking into consideration the two possibilities of sequence pairing in the polypeptide sequence. By knowing these peptide sequences, it is possible, owing to the genetic code, to deduce the corresponding nucleotide sequences. The genetic code is the equivalent of the relation between the nucleotide sequences and the peptide sequences.

Thus, each nucleotide triplet of the nucleotide sequence, or codon, corresponds to a single amino acid. The degeneracy of the genetic code means that several synonymous codons can specify one of the same amino acid. As a consequence, several, nucleotide sequences can be deduced, for a single peptide sequence, owing to the genetic code. Based on this information, degenerate oligonucleotide primers are designed and synthesized: they act as primers for an amplification reaction which leads to a probe with high specificity for the sought nucleic acid(s).

A single primer couple (MadF1/MadR1) has made possible to obtain by PCR and starting from pure genomic DNA of *M. austroafricanum* I-2562, a nucleic acid fragment of 204 by (FIG. 4).

The nucleotide sequence of primer MadF1 is: 5'-GGNTGGGCNTAYGAYCC-3' (SEQ ID NO: 38).

The nucleotide sequence of primer MadR1 is: 5'-GCRT-CRTTYTCRTCSTAST-3' (SEQ ID NO: 39).

The amino acid sequence has been obtained with the aid of the software ORF finder available from the National Center for Biotechnology Information. It is represented by:

```
K Q R G W A Y D P N V R G L P E D T P V T G F T T
P Y L M N N V G G S T M H Y A G H W P R Y K P V D
F R K G T E H G L E G T I D W P I S Y E E L A P Y
Y D K N D (SEQ ID NO: 40).
```

The BLAST analysis of this amino acid sequence confirms that the MpdC protein belongs to the family of the GMC oxidoreductases because the analysis demonstrates 62% similarity (44% identity over 45 amino acids) with a putative choline dehydrogenase from *Bradyrhizobium japonicum*, 53% similarity (38% identity over 76 amino acids) with a glucose dehydrogenase of a strain of *Burkholderia cepacia* and 61% similarity (38% identity over 47 amino acids) with an oxidoreductase, all of which belong to the same family.

2.3. Preparation of a 604 bp Probe

As a result of the information obtained in this first PCR amplification, degenerate primers were designed and synthesized taking into consideration certain conserved motifs which are present in the proteins of the family of the GMC oxidoreductases. One of the primer pairs (MadF2/MadR2) has made it possible to obtain a novel nucleic acid of 604 bp.

The nucleotide sequence of primer MadF2 is: 5'-TTCAC-CTTGTTGGAACCGCTGGG-3' (SEQ ID NO: 41).

The nucleotide sequence of primer MadR2 is: 5'-TCAT-TACCGAGCCGACCTGC-3' (SEQ ID NO: 42).

The probes are labeled with dUTP/digoxigenin (DIG DNA Labelling and Detection Kit; Roche Diagnostics, Laval Canada).

EXAMPLE 3

Cloning of a Nucleic Acid SEQ ID No: 11

3.1. Southern Blot

The Southern blot experiments were carried out with genomic DNA of strain *M. austroafricanum* I-2562 as prepared in example 1.5 µg of genomic DNA is partially digested with the aid of restriction enzymes selected on the basis of their restriction site BamHI, EcoRI, FspI, KnpI, NheI, Nru, PstI, Pvu II or SmaI (wells 2-8, respectively, in FIG. 5). After migration in the gel, the digested DNAs are transferred to a nylon membrane.

This is followed by screening by hybridization of the digested nucleic acids with the aid of the dUTP/digoxigenin-labeled 204 bp probe (DIG DNA Labelling and Detection Kit; Roche Diagnostics, Laval Canada). The 204 bp probe specifically hybridizes with nucleic acid fragments of between 2 and 12 kb (FIG. 5). The positions which correspond to the migration of the DNA of the digoxigenin-labeled molecular weight marker III (Roche; well 1 and well 9) are shown on the left of the luminograph.

3.2. Construction of Mini-Libraries, Screening and Cloning

These nucleic acid fragments are cloned into plasmid pBluescript II KS (pBKS) (+/−) after digestion with SmaI. The recombinant plasmids are used for transforming prepared competent *E. coli* DH10B bacteria (Hanahan, D. et al., *Methods Enzymol.* 1991, 204: 63-113). Each bacterial colony which is obtained from a bacterial clone harboring a recombinant plasmid is transferred onto a nitrocellulose membrane and screened by colony hybridization with the 604 bp probe as obtained in example 2.3. For each positive clone, that is to say each clone which hybridizes with the probe, the recombinant plasmid (pKS1) is extracted and purified with the aid of the QIAprep Spin Miniprep kit (Qiagen, Mississauga, Canada). Given the high degree of instability of the SmaI fragment within plasmid pBKS, which leads to the appearance of plasmids with various sizes, 10 µg of plasmid pBKS1 were digested with SmaI followed by gel extraction. The SmaI band was extracted with the aid of an extraction after migration on a low-melting-point gel. Approximately 600 to 1000 base pairs were obtained in each extraction, and, consequently, about twelve extractions were necessary to obtain a complete sequence. After the sequencing had been analyzed, with the 5' part upstream of the mpdC gene missing, a new mini-library was established in order to obtain a 5.6 kb PstI fragment, using the same techniques as above, but using the 914 bp probe which overlaps with the first insert and is obtained with the aid of the primer pair MF3/MR3. Plasmid pKS3 was isolated from a positive clone developed by "colony hybridization" (FIG. 6). The PstI-PstI fragment detected by the probe has thus been cloned in accordance with the same protocol as above in order to obtain a recombinant plasmid pKS3.

The whole of the PstI insert which is present in this plasmid was sequenced in accordance with the primer-walking technique with the aid of a T7 DNA polymerase (T7-DNA sequencing kit, Applied Biosystems, Foster City, Calif.) and a sequencer (ABT prism 377 automated fluorescence sequencer; Applied Biosystems, Foster City, Calif.). The nucleotide sequences and the corresponding amino acids were compared with those present in the EMBL, Swissprot and GenBank databases using the BLASTN and BLASTX software of the National Center for Biotechnology Information (NCBI).

EXAMPLE 4

Identification and Characterization of Different Open Reading Frames (ORFs) in the Sequence SEQ ID No: 11 of *M. austroafricanum* I-2562

The analysis of open reading frames present in the PstI/SmaI DNA sequence SEQ ID No: 11 obtained from the two cloning steps described in example 3 was performed with the aid of the "ORF finder" software. Five coding sequences have been identified: SEQ ID No: 1, SEQ ID No: 3, SEQ ID No: 5, SEQ ID No: 7 and SEQ ID No: 9; they code for the polypeptides SEQ ID No: 2, SEQ ID No: 4, SEQ ID No: 6, SEQ ID No: 8 and SEQ ID No: 10, respectively (cf. table hereinbelow).

| Nucleotide sequence | ORF | Amino acid sequence of the polypeptide | Name of polypeptide | Molecular weight |
|---|---|---|---|---|
| SEQ ID No: 1 1515 bp | mpdC | ID No: 2 552 amino acids | MpdC | 55 kDa |
| SEQ ID No: 3 648 bp | orf1 | SEQ ID No: 4 215 amino acids |  | 27 kDa |
| SEQ ID No: 5 1659 bp | mpdB | SEQ ID No: 6 552 amino acids | MpdB | 64 kDa |
| SEQ ID No: 7 672 bp | orf2 | SEQ ID No: 8 223 amino acids |  | 25 kDa |
| SEQ ID No: 9 1233 bp | mpdR | SEQ ID No: 10 410 amino acids | MpdR | 47 kDa |

It has thus been possible to correlate the amino acid sequence SEQ ID No: 6 of the 64 kDa MpdB polypeptide with the first polypeptide sequences and the 204 and 604 bp PCR amplifications. This mpdB gene is present in a genetic arrangement comprising 3 other ORFs in the same orientation, mpdC, orf1 and orf2 which code for the 55, 27 and 25 kDa proteins, respectively. Upstream of this cluster, a novel gene which is in the opposite orientation to the first cluster and codes for a 47 kDa protein has been identified and named mpdR. The arrangement of this system is shown diagrammatically in FIG. 7.

4.1. ORF mpdC, SEQ ID No: 1

The analysis with the BLAST software which is shown in FIG. 13, shows a high degree of similarity with a large number of dehydrogenases which belong to the family of the aldehyde dehydrogenases. The polypeptide SEQ ID No: 2 which is encoded by this ORF corresponds to a 55 kDa polypeptide whose expression is induced on MTBE. This polypeptide is capable of dehydrogenating hydroxybutyraldehyde to give HIBA.

Result obtained with the "NCBI domain search" software:

| | |
|---|---|
| Aldedh, Aldehyde dehydrogenase family | e-value = 3e−114 |
| PutA, NAD-dependent aldehyde dehydrogenases | e-value = 5e−106 |
| COG4230, Delta 1-pyrroline-5-carboxylate dehydrogenase | e-value = 3e−44 |

4.2. ORF orf1, SEQ ID No: 3

The polypeptide SEQ ID No: 4 which is encoded by this ORF corresponds to a 27 kDa polypeptide whose expression is induced on MTBE.

4.3. ORF mpdB, SEQ ID No: 5

The polypeptide SEQ ID No: 6 which is encoded by this ORF corresponds to a 64 kDa polypeptide whose expression is induced on MTBE. A high degree of similarity exists with a large number of oxidases and dehydrogenases which belong to the family of the GMC (glucose-methanol-choline) oxidoreductases. More precisely, the analysis with the "NCBI Conserved Domain Search" software has detected similarities with the protein encoded by the betA gene, which codes for the choline dehydrogenase which belongs to the same family. The amino acid sequence deduced can be correlated with the N-terminal sequence and the two internal sequences of the 64 kDa protein which is induced specifically on MTBE and which is responsible for the transformation of 2-M-1,2-PD into hydroxybutyraldehyde. See FIG. 14.

NCBI conserved domain search result

| | |
|---|---|
| BetA, Choline dehydrogenase and related flavoproteins | e-value = 3e−48 |
| KOG1238, Glucode dehydrogenase/choline dehydrogenase | e-value = 2e−07 |
| KOG1335, Dihydrolipoamide dehydrogenase [Energy production] . . . | e-value = 6e−05 |
| GMC_oxred_N, GMC oxidoreductase | e-value = 2e−03 |
| GMC_oxred_C, GMC oxidoreductase | e-value = 4e−03 |

4.4. ORF orf2, SEQ ID No: 7

The polypeptide SEQ ID No: 8 which is encoded by this ORF corresponds to a 25 kDa polypeptide. BLAST analysis has shown a homology with a di/tripeptide permease (COG3104: Dipeptide/tripeptide permease [*Rubrivivax gelatinosus* PM1] Length=372, Expect=2e-24). The analysis of the hydropathy of this protein with the software "Predict Protein" has revealed the presence of 5 transmembrane segments. See FIG. 15.

The expression of this polypeptide is probably induced in the presence of MTBE.

This protein is thus found in the membrane of bacteria of the species *M. austroafricanum*.

4.5. ORF mpdR, SEQ ID No: 9

The polypeptide SEQ ID No: 10 which is encoded by this ORF corresponds to a 47 kDa polypeptide. This ORF is located upstream of the four previous ORFs and is orientated in the other direction as shown in FIG. 7. BLAST analysis reveals a similarity of the first half of the sequence with a large number of σ54 transcriptional regulators, in particular of the AcoR type:

| | |
|---|---|
| Sigma-54 dependent transcriptional activator [*Azoarcus* sp. EbN1] | e = 6e−23 |
| COG3284, AcoR Transcriptional activator of acetoin/glycerol metabolism | e = 1e−22 |

According to these analyses, it is not possible to detect if the expression of this polypeptide is induced specifically or not on the MTBE profile, but it is possible to detect its expression in an RT-PCR analysis. Potentially, if plays a role in the regulation of the expression of mpd genes.

EXAMPLE 5

Expression of the mpd Gene Cluster by RT-PCR 5.1. Extraction of the mRNA of *M. austroafricanum* I-2562

For the RNA extraction experiments, all tools, all solutions and the vessels were prepared so as to avoid contamination with RNases following standard procedures (Sambrook et al., *Molecular Cloning: A Laboratory Manual*. Cold Spring Harbor Laboratory Press, Cold Spring Harbor, N.Y. 2001).

The total RNA of *M. austroafricanum* I-2562 was extracted with 20 mL of a culture with an $OD_{600\ nm}$ of 0.7. After incubation on ice for 30 min, the cells were centrifuged (8000×g for 10 min at 4° C.) and maintained on ice. Thereafter, 600 μL of lysozyme (Roche Diagnostics, Laval, Canada) at a concentration of 3 $mg \cdot mL^{-1}$ and 600 μL of lysostaphin (Sigma, St-Louis, Mo.) at a concentration of 50 $\mu g \cdot mL^{-1}$ were added to the cell pellet, and the mixture is incubated for 10 min at 37° C. Thereafter, 10 ml of RNAwiz™ (Ambion, Austin, Tex.) were added, and the mixture is vortexed for 15 sec. The mixture is then divided between 2 mL tubes (1400 μL/tube) containing 250 mg of zirconium-silica beads (0.1 mm diameter), placed into a vortex adaptor (Ambion) and vortexed for 10 min. After centrifugation (13000×g at 4° C. for 5 min), the bacterial lysate which corresponds to the supernatants of each tube is transferred into fresh 2 mL tubes, and 0.2 volume of $CHCl_3$ is added to each tube. The tubes are then vortexed for 30 sec, incubated at room temperature for 10 min and then centrifuged (13000×g at 4° C. for 5 min), and the supernatants were then transferred into fresh 2 ml, tubes. The RNA extracts are precipitated by sequential addition of 0.5 volume of DEPC-treated $H_2O$, 1 volume of isopropanol and ⅕₀ volume RNase-free glycogen at a concentration of 5 $mg \cdot mL^{-1}$ (Ambion), mixed thoroughly and incubated for 10 min at room temperature. The RNA is centrifuged (13000×g at 4° C. for 5 min), washed twice with 70% ethanol, dried for 30 sec (DNA Speed Vac, Savant) and resuspended in DEPC $H_2O$ (25 μL/tube). The RNA quality was determined by electrophoresis with the aid of a 1% strength non-denaturing agarose gel in an 0.5× TBF buffer (Trizma Base 45 mM, 45 mM boric acid, 1 mM $Na_2EDTA$, pH=8.3). The RNA is precipitated with 1/10 volume of 3M sodium acetate, pH=7.0, and 2.5 volume of 95% ethanol and then kept at −80° C.

5.2. Treatment with DNase, and Reverse-Transcriptase PCR (RT-PCR)

Two mg of RNA extracted from *M. austroafricanum* I-2562 were treated with the "DNA-Free" kit (Ambion, Austin, Tex.) in accordance with the manufacturer's recommendations. The elimination of the DNA was verified by PCR amplification using specific primers generated within the mpd cluster and by electrophoresis on 1% agarose gel. The final RNA concentration was determined quantitatively at 260 nm with the aid of a Nanodrop (Nanodrop Technologies, Wilmington, USA). The reverse-transcriptase PCR (RT-PCR) experiments were carried out in accordance with, the "One step RT-PCR" protocol of the kit from Qiagen (Qiagen, Mississauga, Canada) as described by the manufacturer. 120 ng of RNA are used for each RT-PCR attempt while carrying out each time a positive (and negative) control PCR amplification with (or without) 100 ng of gDNA from *M. austroafricanum* I-2562 in parallel. The RT-PCR conditions are described hereinbelow.

Reverse Transcription Step:

1) 30 min at 50° C.

2) ∞ at 50° C.

PCR Step:

15 min at 95° C.

30 to 40 cycles (variables depending on the intensity of the signal):

1) 30 sec at 94° C.

2) 1 min at 55° C.

3) 1 min at 72° C.

Final Elongation Step:

1) 10 min at 72° C.

2) ∞ at 4° C.

5.3. Expression of the mpd Gene Cluster by RT-PCR During the Growth of *M. austroafricanum* I-2562 on TBA The expression of the mpd genes is tested after the bacteria were grown on TBA, the main intermediate of the MTBE biodegradation (see FIG. 1). Primer pairs overlapping with the different mpd genes are generated (see table hereinbelow) in order to verify that the mRNA which corresponds to this cluster was transcribed into a monocistron. The total RNA is extracted from the cultures after growth on TBA, and the RT-PCR reactions are carried out with the different primers. The result of these experiments is shown in FIG. 8 and demonstrates that the transcription of the mpd gene cluster is very likely to be monocistronic; the genes being organized as an operon. (Ma et al. *J. Bacteriol.*, 2002, 184: 5733-5745).

Table: Primers used in all of the PCR and RT-PCR amplification experiments:

| Primers | Sequence | Amplified region |
|---|---|---|
| Bott1 (SEQ ID N: 15) | 5'-TGCACACAGGCCACAACCCA-3' | ADNr 16S |
| Bott2 (SEQ ID N: 16) | 5'-GAGAGTTTGATCCTGGCTCAG-3' | ADNr 16S |
| 244 (SEQ ID N: 17) | 5'-CCCACTGCTGCCTCCCGTAG-3' | ADNr 16S |
| Tb11 (SEQ ID N: 18) | 5'-ACCAACGATGGTGTGTCCAT-3' | hsp65 |
| Tb12 (SEQ ID N: 19) | 5'-CTTGTCGAACCGCATACCCT-3' | hsp65 |
| MaFV2 (SEQ ID N: 20) | 5'-GTCTAATACCGAATACACCCTTC T-3' | ADNr 16S |
| MaRV6 (SEQ ID N: 21) | 5'-GTAGTTGGCCGGTCCTTCTTCTC C-3' | ADNr 16S |
| MF1 (SEQ ID N: 22) | 5'-TGAGAAGCCTCGTGTATTAC-3' | orf1-mpdB |
| MR1 (SEQ ID N: 23) | 5'-GAGATAAGGCGTGGTGAA-3' | orf1-mpdB |
| MF2 (SEQ ID N: 24) | 5'-AGTGACGGCACCCATAAGTG-3' | mpdR internal |
| MR2 (SEQ ID N: 25) | 5'-TCGAGGTGTTGAGGTCCGAAT-3' | mpdR internal |
| MF3 (SEQ ID N: 26) | 5'-ATCATCCCGTGGAACTAC-3' | mpdC internal |
| MR3 (SEQ ID N: 27) | 5'-TGACCTGGGCGATGTGTT-3' | mpdC internal |
| MF4 (SEQ ID N: 28) | 5'-ATCAGACCTGGGATGTGC-3' | mpdB-orf2 |
| MR4 (SEQ ID N: 29) | 5'-GGCTGTGAAAGTCGGATGA-3' | mpdB-orf2 |
| RT-PCR-F1 (SEQ ID N: 30) | 5'-AGTGACGGCACCCATAAGTG-3' | mpdR internal |
| RT-PCR-R1 (SEQ ID N: 31) | 5'-TCGAGGTGTTGAGGTCCGAAT-3' | mpdR internal |
| RT-PCR-F2 (SEQ ID N: 32) | 5'-GCAGGTCGGCTCGGTAATGA-3' | mpdC-orf1 |
| RT-PCR-R2 (SEQ ID N: 33) | 5'-GTAATACACGAGGCTTCTCA-3' | mpdC-orf1 |
| RT-PCR-F3 (SEQ ID N: 34) | 5'-ACGGTCTCGTCGGCAAATAC-3' | mpdB-orf2 |
| RT-PCR-R3 (SEQ ID N: 35) | 5'-GCACATCCCAGGTCTGAT-3' | mpdB-orf2 |

EXAMPLE 6

Expression of mpd Genes in the Bacterium of Strain *M. smegmatis* mc2 155

6.1. Construction of the Expression Vector Comprising the mpd Genes, and Transformation of Bacteria The genes comprised in the genetic arrangement mpd were inserted into the vector pCL4D in two stops (Picardeau et al., *Microbiology*, 2000, 146: 305-313). Firstly, the NotI-NotI fragment with the lengths of 4401 base pairs which is present in plasmid pKS1 was digested with NotI (NEB, Pickering, Canada) and cloned into the HindII site of pCL4D. Chemically competent *E. coli* DH10B cells were used for the transformation, and the selection of transformants on LB-medium containing 20 μg·mL$^{-1}$ kanamycin. Positive clones containing the recombinant plasmid p4D1 are detected by PCR amplification with the aid of the forward and reverse primers (table in example 5). During the second step, the 5574 bp PstI fragment which contains the missing part of the mpdC gene, the mpdR gene and the orf3 was extracted by digesting plasmid pKS3 with the aid of the enzyme PstI. This fragment was introduced into plasmid p4D1 which had previously been digested with PstI, which made it possible to remove the PstI fragment which corresponds to the 914 bp probe present in plasmid p4D1. The orientation of the PstI fragment in the recombinant plasmid p4D2 containing all of the mpd cluster was verified by PCR.

To express all of the cloned genes, vector p4D2 was introduced into competent cells of strain *M. smegmatis* mc2 155 using the electroporation technique. One transformant (strain *M. smegmatis* mc2 155-clone 9) which was obtained in this transformation was isolated on an LB dish containing kanamycin (20 µg·mL$^{-1}$). Plasmid pCL4D, which does not comprise the insert, was also introduced into bacteria of strain M. smegmatis mc2 155 (strain M. smegmatis mc2 155-pCL4D) and acts as the control.

6.2. Functional Expression of the mpdB and mpdC Genes in M. smegmatis mc2 155

M. smegmatis mc2 155-clone 9 bacteria (with insert) and M. smegmatis mc2 155-pCL4D bacteria (control) are maintained on LB medium containing 20 mg·L$^{-1}$ kanamycin. The two strains are grown for 72 h at 30° C. on 200 mL of LB medium containing 20 mg·L$^{-1}$ kanamycin. The cells of M. smegmatis mc2 155-clone 9 and M. smegmatis mc2 155-pCL4D are harvested by centrifugation (13 000 g for 15 min), washed twice and suspended in 40 ml, of phosphate buffer (20 mM, pH 7) containing the substrate to be tested. (MTBE, TBA, 2-M-1,2-PD or HIBA) in sealed 120-mL-vials. After seeding, the vials are incubated at 37° C. on a rotary shaker. Where necessary, chloramphenicol is added from a solution in water which has been filter-sterilized (0.22 µm) in order to obtain a final concentration of 400 mg/L$^{-1}$. The filtered samples of these cultures are analyzed by GC or HPLC. The degradation of the substrate is monitored over a period of 24 h. The specific activities (mg degraded substrate·g$^{-1}$ biomass·h$^{-1}$) are calculated on the basis of the maximum degradation rates.

6.3. Expression in M. smegmatis mc2 155 of the mpd Gene Cluster Isolated from M. austroafricanum I-2562

A 9.1 kb fragment, SEQ ID No: 11 containing the mpd gene cluster of M. austroafricanum I-2562 was cloned into plasmid pCL4D (Picardeau et al. 2000). This plasmid, named p4D2, was subsequently used for transforming M. smegmatis mc2 155. The transformation was also carried out with plasmid pCL4D as the control. Two transformants were selected: M. smegmatis mc2 155-clone 9 (containing p4D2 and thus harboring the mpd genes) and M. smegmatis mc2 155-pCL4D (harboring the vector, pCL4D). The two strains are grown on LB medium containing kanamycin, and subsequently tested in experiments in resting cells for the ability of degrading MTBE, TBA, 2-M-1,2-PD and HIBA. With strains M. smegmatis mc2 155-clone 9 and M. smegmatis mc2 155-pCL4D, no degradation of MTBE, of TBA or of HIBA was observed (table 2).

The degradation of 2-M-1,2-PD and the stoichiometric production of HIBA (312.1±2.3 µM degraded and 311.6±4.5 µM product, respectively) were only observed in the presence of strain M. smegmatis mc2 155-clone 9 (FIG. 9). No degradation of 2-M-1,2-PD was observed in the presence of strain M. smegmatis mc2 155-pCL4D or in the abiotic control. When two strains were grown on complete LB medium, the induction of genes was necessary to produce the corresponding enzymes, and this is why degradation does not set on before 4 hour's incubation in the presence of 2-M-1,2-PD. No degradation of 2-M-1,2-PD is observed when the cells of M. smegmatis mc2 155-clone 9 are incubated in the presence of 2-M-1,2-PD and chloramphenicol, which is known to inhibit the translation of mRNA into proteins.

The maximum degradation rate of 2-M-1,2-PD by strain M. smegmatis mc2 155-clone 9 was calculated and is 2.34±0.41 µmol·g$^{-1}$ (dry weight)·min$^{-1}$.

EXAMPLE 7

Identification of a Novel Strain M. austroafricanum I-3401, which is Capable of Growth on MTBE Surface water taken from the bottom of a storage tank of an MTBE-supplemented petrol was used for seeding MM mineral medium containing 200 mg·L$^{-1}$ MTBE. The MTBE was slowly, but fully, utilized in 140 days. All bacteria which formed colonies alter streaking out on dishes with LB medium plates were reisolated individually and then tested for their ability to grow on MM containing MTBE as single carbon and energy source. One strictly aerobic Gram-positive bacterium which forms rods and grows in the form of yellow colonies on LB medium dishes was isolated and has proved to be capable of growing on MTBE.

The 16S rDNA of strain I-3401 was fully sequenced on both strands, and the gene hsp65 was partially sequenced. The sequence of the 16S rDNA demonstrates that the novel strain I-3401, SEQ ID No: 13, is very close to M. austroafricanum I-2562, with seven different nucleotides (5 substitutions and 2 insertions in I-3401). The sequence of the gene hsp65 differs by eight nucleotides from the sequence of gene hsp65 of the typical strain (reference) of M. austroafricanum. The ability of M. austroafricanum I-3401 to grow on MTBE was demonstrated (FIG. 10).

EXAMPLE 8

Generation of Primers with Specificity for the 16S rDNA of M. austroafricanum, and Specific PCR Conditions 8.1. Analyses of the 16S rDNA and of Gene hsp65 of Strain M. austroafricanum I-2562

To identify the novel strain I-3401, a PCR amplification of the 16S rDNA was carried out using the primer pair Bott 1 forward/Bott 2 reverse (see table of example 5). The amplification, product was purified using the Qiagen kit (Qiagen, Mississauga, Ontario, Canada) and the nucleotide sequencing was carried out using the primer 244 (see table of example 5). The PCR amplification of the hsp65 gene was carried out using the forward primer Tb 11 and the reverse primer Tb 12 (see table of example 5). The amplification product was purified with the Qiagen kit and sequencing was carried out using the primer Tb 11. The sequencing reaction is carried out with the BigDye cycle terminator sequencing kit (Version 3.1, Applied Biosystems, Foster City, Calif., USA) as described by the manufacturer using 25 ng of purified DNA and 15 µmol of the universal primers used for sequencing the 16S rDNA of Eubacteria. The reaction is programmed as follows: 25 cycles of 10 sec at 96° C., 5 sec at 50° C., and 4 min at 60° C. The sequencing products are purified on Centri-Sep columns as described by the manufacturer (Princeton Separations, Inc., Adelphia, N.J., USA) in order to eliminate surplus terminators. The sequencing reactions are carried out using an ABT Prism 377 automated fluorescence sequencer (Applied Biosystems, Foster City, Calif.). The nucleotide sequences obtained are compared with those in the EMBL/GenBank gene database, and the identities are evaluated, using the BLAST alignment system (Altschul et al., 1997).

8.2. Generation of PCR-Specific Conditions and Primers

The 16S rDNA sequences of M. austroafricanum I-2562 and of related mycobacterial species are aligned, and the conserved and variable sequences are compared. On the basis of analyses of these multiple alignments, various primer pairs which are specific for the species M. austroafricanum are compared with the available 16S rDNA sequences using the BLAST database search program (Altschul et al. Nucleic

*Acids Res.,* 1997, 25: 3389-3402). These sequences were also analyzed in order to determine their denaturation temperature (TM), the possibility of forming dimers, and their (G+C) content, using the Amplify software. The most efficient primer pair was: MaFV2 forward and MaRV6 reverse (see table of example 5). The expected size of the PCR product is 331 bp.

The PCR reactions are carried out in the following manner: each tube contains 5 μL of genomic DNA obtained by boiling lysis for 10 min of colonies isolated from dishes freshly streaked with strains of the collection, the strains of *Mycobacterium austroafricanum* or the samples from a biobarrier seeded with *M. austroafricanum* I-2562, 2.5 units of Taq DNA polymerase (Amersham Pharmacia Biotech), 5 μL of 10× dilute Taq DNA polymerase buffer (Amersham pharmacia biotech), 25 pmol of each primer, 4 μL of 2.5 mM deoxyribonucleotide triphosphates (200 μM of each: dATP, dGTP, dCTP and dTTP), 2 μL of 25 mM MgCl$_2$, and sterile distilled water to a final volume of 50 μL. The negative control contains the same mixture as described hereinabove with the exception that the DNA is replaced by sterile water. The samples are heated beforehand for 3 min at 95° C. in a Bio-Rad Thermal iCycler apparatus (Bio-Rad, Mississauga, Ontario, Canada), and then the temperature is lowered to 80° C. before they are added to the enzyme mixture Taq DNA polymerase/10× dilute buffer. In order to obtain specific amplification conditions, the amplification conditions are as follows: 30 sec at 94° C., 1 min at 68° C., 1 min at 72° C., repeated over 30 cycles, and the final extension is carried out at: 72° C. for 7 min. The PCR tubes are maintained at 4° C. until the point in time when the agarose gel electrophoresis is carried out. 10 μL of each of the PCR products are mixed with 2 μl of loading buffer comprising 30% (v/v) glycerol, 0.15% (w/v) bromophenol blue, 0.15% (w/v) xylene cyanole. The different PCR products thus prepared and the 1 kb DNA marker GeneRuler™ (MBI Fermentas, Inc., Burlington, Ontario, Canada) are applied on 1% (w/v) agarose gel prepared with TAE. After the migration, the gel is stained with ethidium bromide and developed with UV rays at 254 nm on a trans illuminator. The gels are photographed using a Polaroid film type 57.

EXAMPLE 9

Detection of the Presence of the mpd Gene Arrangement in the Novel Strain *M. austroafricanum* I-3401

Since the biodegradation of MTBE by strain *M. austroafricanum* I-3401 was similar to that of *M. austroafricanum* I-2562, the presence, or absence, of the mpd cluster in the novel strain was studied. Thus, primer pairs MF1/MR1, MF2/MR2, MF3/MR3 and MF4/MR4 which specifically amplify in different genes of the mpd cluster were generated (table of example 5). PCR amplifications on genomic DNA of *M. austroafricanum* I-3401 or I-2562 (the latter one as the positive control) were carried out (FIG. 11) and show positive amplifications for all primer pairs. This demonstrates the presence of a genetic arrangement similar to that of the mpd genes of *M. austroafricanum* I-2562 in the genome of the novel strain *M. austroafricanum* I-3401. It is therefore likely that the novel strain uses the same reaction pathway for assimilating 2-M-1,2-PD during the MTBE catabolism.

EXAMPLE 10

Specific Detection of *M. austroafricanum* I-2562 and I-3401 by PCR

The primers MaFV2 and MaRV6 which are specific of the species *M. austroafricanum* were generated (see table of example 5). The specificity of these primers which anneal in two variable regions V2 and V6 of the 16S rDNA of *M. austroafricanum* I-2562 was evaluated using genomic DNA of more or less closely related strains. The results shown in FIG. 12 demonstrate that only the genomic DNAs of two strains of *M. austroafricanum*, viz. I-2562 and I-3401, which metabolize MTBE, allow a positive PCR amplification to be obtained. With these primers it is thus possible to specifically detect microorganisms of this species. Other microorganisms of the genus *Nocardiaceae* show no PCR amplification.

EXAMPLE 11

Comparison Between Strains I-2562 and I-3401

|  | *M. austroafricanum* | |
| --- | --- | --- |
|  | I-2562 | I-3401 |
| Ability of degrading ETBE (130 mg/l) | 100 days | 33 days |
| MTBE metabolism: assimilation of intermediates | — | Accumulation of 2-M-1,2-PD |
| 2-Methyl-1,2-propanediol degradation rate | 413 mg · g$^{-1}$ dry weight · h$^{-1}$ | 60 mg · g$^{-1}$ dry weight sec · h$^{-1}$ |

An important difference between strain I-2562 and strain I-3401 is their ability of degrading ETBE: at an equivalent ETBE concentration (130 mg/L), *M. austroafricanum* I-2562 degrades ETBE within 100 days while I-3401 performs this degradation three times more rapidly. On the other hand, the degradation rate of 2-M-1,2-PD, when used directly as the substrate, is approximately 7 times more rapid in I-2562 than in I-3401. Finally, it is possible to detect the presence of 2-M-1,2-PD during the degradation of tert-butyl alcohol (TBA) in I-3401 due to this difference in the degradation rate of 2-M-1,2-PD.

The invention claimed is:

1. An isolated or purified polypeptide with an activity in the degradation pathway of methyl tert-butyl ether (MTBE) and/or at least one of the catabolites of MTBE, said polypeptide having aldehyde dehydrogenase activity, and said polypeptide comprising the amino acid sequence of SEQ ID No: 2.

2. The polypeptide as claimed in claim 1, wherein the polypeptide is isolated and/or purified from a bacterial strain capable of growing in a medium comprising MTBE and/or at least one of the catabolites of MTBE.

* * * * *

SEQUENCE LISTING

<160> NUMBER OF SEQ ID NOS: 42

<210> SEQ ID NO 1
<211> LENGTH: 1515
<212> TYPE: DNA
<213> ORGANISM: Mycobacterium austroafricanum

<400> SEQUENCE: 1
atgacccgaa ctctctcggc tgatgccgac acccgcacgg cgacacctcc gctgatgtac    60

```
gtcaacggcg agtggctgcc cgcccgcagt ggggccacct ttcccaccat cgaacccagc      120
acgggtcgac cgatcactga gattccccgc ggggactcga gcgatgtgga cgcggcggtg      180
aaagccgctg ccgacgtggc cgttgagtgg cagttcaccg atgccatcac ccgcgccgcc      240
ctgctcaggc gattggcgga gctggtggca gagaacgccg aggagctggc gcggatcgag      300
tcgctggact cggtcactca tctggcgaag gcgcgtgaac tggtgaccgc gatacccctg      360
tggctcgagt actgggccgg cgcagctgac aaagtgggcg ccgcaccat cgctgtaccg       420 ggtaacaaac tcagcttcac cttgttggaa ccgctgggcg tcaccgcgca catcatcccg      480
tggaactacc cgctgttgat ccttgctcgg tccatcgccc cggcactcgc attgggcaac      540
acctgtgtcg tcaagcccgc tgaggacacg tccctgtcag cgctgaagtt cgccgagctg      600
gtacacgccg ccggttttcc cgccggagtg ttcaatgtgg tgaccggtta cggttccgaa      660
gccggcgcgg ctcttgccgc tcaccccgag gtgcgcggaa tcaccttcac cggttcgacc      720
gagaccgggc gggagatcgc ccgactgggc ggccaacaca tcgcccaggt caacctggaa      780
ctcggcggga agagcccgtt ggtcgtcttt cccgacgcgc cgctcgaaga cgccgtagag      840
gtggccgtac agggcttctg ctcacgggca gggcaagtgt gtgtcgccgg gagccggctc      900
ttcctccatg aggacatcgc cgaccggttc ctcgagatgc tcgtttcgcg actcgagact      960
gtcaccgtcg gcgacccgtt cgacggtgcg acccagatgg gtccgctcgc ctcgaagaag     1020
cactacgacc gtgtgcgtga gtacatcgag gtcgggaagc aggaggcgac cctgctctac     1080
ggcggcggtc ggccgacgga cacgcccgat gacgggttct tcgtcgagcc aacggttttc     1140
gtcgacgtcg caacggatgc gcggatcgca cgcgaggaga tcttcgggcc cgtcacagcg     1200
gtgatgcggt ggtcatcggt cgacgatctg atcgccacca tcaatgattc ggaattcggt     1260
ctcttcgctg tgctctggtg ccgggacatc accagtgcgc tggacacggc gaaacgcctg     1320
caggtcggct cggtaatgat caacgactgg ttcggtgagc tgccgatgac tccgcacgga     1380
ggccacaagc aaagcggcac cggacgcgag gaaggcctcg aagcggtaca cggctacaca     1440
caggtcaagc acatcggcat caacctcgag ccgtcgcccg caaagtccgc cgattgggcc     1500
ggtgcacctc tgtga                                                      1515
```

<210> SEQ ID NO 2
<211> LENGTH: 504
<212> TYPE: PRT
<213> ORGANISM: Mycobacterium austroafricanum

<400> SEQUENCE: 2

```
Met Thr Arg Thr Leu Ser Ala Asp Ala Asp Thr Arg Thr Ala Thr Pro
1               5                   10                  15

Pro Leu Met Tyr Val Asn Gly Glu Trp Leu Pro Ala Arg Ser Gly Ala
            20                  25                  30

Thr Phe Pro Thr Ile Glu Pro Ser Thr Gly Arg Pro Ile Thr Glu Ile
        35                  40                  45

Pro Arg Gly Asp Ser Ser Asp Val Asp Ala Ala Val Lys Ala Ala Ala
    50                  55                  60

Asp Val Ala Val Glu Trp Gln Phe Thr Asp Ala Ile Thr Arg Ala Ala
65                  70                  75                  80

Leu Leu Arg Arg Leu Ala Glu Leu Val Ala Glu Asn Ala Glu Glu Leu
                85                  90                  95

Ala Arg Ile Glu Ser Leu Asp Ser Gly His Tyr Leu Ala Lys Ala Arg
            100                 105                 110
```

```
Glu Leu Val Thr Ala Ile Pro Leu Trp Leu Glu Tyr Trp Ala Gly Ala
            115                 120                 125

Ala Asp Lys Val Gly Gly Arg Thr Ile Ala Val Pro Gly Asn Lys Leu
    130                 135                 140

Ser Phe Thr Leu Leu Glu Pro Leu Gly Val Thr Ala His Ile Ile Pro
145                 150                 155                 160

Trp Asn Tyr Pro Leu Leu Ile Leu Ala Arg Ser Ile Ala Pro Ala Leu
                165                 170                 175

Ala Leu Gly Asn Thr Cys Val Val Lys Pro Ala Glu Asp Thr Ser Leu
            180                 185                 190

Ser Ala Leu Lys Phe Ala Glu Leu Val His Ala Ala Gly Phe Pro Ala
        195                 200                 205

Gly Val Phe Asn Val Val Thr Gly Tyr Gly Ser Glu Ala Gly Ala Ala
        210                 215                 220

Leu Ala Ala His Pro Glu Val Arg Gly Ile Thr Phe Thr Gly Ser Thr
225                 230                 235                 240

Glu Thr Gly Arg Glu Ile Ala Arg Leu Gly Gly Gln His Ile Ala Gln
                245                 250                 255

Val Asn Leu Glu Leu Gly Gly Lys Ser Pro Leu Val Val Phe Pro Asp
            260                 265                 270

Ala Pro Leu Glu Asp Ala Val Glu Val Ala Val Gln Gly Phe Cys Ser
        275                 280                 285

Arg Ala Gly Gln Val Cys Val Ala Gly Ser Arg Leu Phe Leu His Glu
    290                 295                 300

Asp Ile Ala Asp Arg Phe Leu Glu Met Leu Val Ser Arg Leu Glu Thr
305                 310                 315                 320

Val Thr Val Gly Asp Pro Phe Asp Gly Ala Thr Gln Met Gly Pro Leu
                325                 330                 335

Ala Ser Lys Lys His Tyr Asp Arg Val Arg Glu Tyr Ile Glu Val Gly
            340                 345                 350

Lys Gln Glu Ala Thr Leu Leu Tyr Gly Gly Gly Arg Pro Thr Asp Thr
        355                 360                 365

Pro Asp Asp Gly Phe Phe Val Glu Pro Thr Val Phe Val Asp Val Ala
370                 375                 380

Thr Asp Ala Arg Ile Ala Arg Glu Glu Ile Phe Gly Pro Val Thr Ala
385                 390                 395                 400

Val Met Arg Trp Ser Ser Val Asp Asp Leu Ile Ala Thr Ile Asn Asp
                405                 410                 415

Ser Glu Phe Gly Leu Phe Ala Val Leu Trp Cys Arg Asp Ile Thr Ser
            420                 425                 430

Ala Leu Asp Thr Ala Lys Arg Leu Gln Val Gly Ser Val Met Ile Asn
        435                 440                 445

Asp Trp Phe Gly Glu Leu Pro Met Thr Pro His Gly His Lys Gln
        450                 455                 460

Ser Gly Thr Gly Arg Glu Glu Gly Leu Glu Ala Val His Gly Tyr Thr
465                 470                 475                 480

Gln Val Lys His Ile Gly Ile Asn Leu Glu Pro Ser Pro Ala Lys Ser
                485                 490                 495

Ala Asp Trp Ala Gly Ala Pro Leu
            500

<210> SEQ ID NO 3
<211> LENGTH: 648
```

```
<212> TYPE: DNA
<213> ORGANISM: Mycobacterium austroafricanum

<400> SEQUENCE: 3
atgcctcaag aagacgcctt ggtgagcgcc ccattcgggg cgccgtcctt gggggaagat      60
cgtcccgatc aaccccattt cgagaccggc cgaccgagac tcggcggact ggtcgccccc     120
gtcgcgtttg atgagctcga ggcagcggtc atcgacgccc tggccgacac gatgatcccc     180
gccgaaggcg gctttccggc cgcaagcgac gtgggaatcg tcgatttctt cggccgctac     240
acgactccca ccggattccg cgcgaagcac ttcccctacc tcgaaggga caagttgaag      300 agcgcactcg cggggctcgg cgaagaattc gtcaacgccg acaccgatac gcgcacccag     360
gcggtcctcc gattggagaa ggacgatgag gagttcttcg cgcaggtgag aagcctcgtg     420
tattacggct actactccgc gaacgcagtg accgtcgcca ttcaccagca gattccggcc     480
gggcgcgact accacggacc cccactcccc tacggctatc tgcattgcat cgaggactgg     540
gatgaagcgg cgctctccac atcggggcag ggctcaggct atgtcgccac cgacgatgtg     600
gtccgagtgg atctcagcaa actcacctgg ctgaacaaca agacttga                  648

<210> SEQ ID NO 4
<211> LENGTH: 215
<212> TYPE: PRT
<213> ORGANISM: Mycobacterium austroafricanum

<400> SEQUENCE: 4

Met Pro Gln Glu Asp Ala Leu Val Ser Ala Pro Phe Gly Ala Pro Ser
1               5                   10                  15

Leu Gly Glu Asp Arg Pro Asp Gln Pro His Phe Glu Thr Gly Arg Pro
                20                  25                  30

Arg Leu Gly Gly Leu Val Ala Pro Val Ala Phe Asp Glu Leu Glu Ala
            35                  40                  45

Ala Val Ile Asp Ala Leu Ala Asp Thr Met Ile Pro Ala Glu Gly Gly
        50                  55                  60

Phe Pro Ala Ala Ser Asp Val Gly Ile Val Asp Phe Phe Gly Arg Tyr
65                  70                  75                  80

Thr Thr Pro Thr Gly Phe Arg Ala Lys His Phe Pro Tyr Leu Glu Glu
                85                  90                  95

Asp Lys Leu Lys Ser Ala Leu Ala Gly Leu Gly Glu Glu Phe Val Asn
                100                 105                 110

Ala Asp Thr Asp Thr Arg Thr Gln Ala Val Leu Arg Leu Glu Lys Asp
            115                 120                 125

Asp Glu Glu Phe Phe Ala Gln Val Arg Ser Leu Val Tyr Tyr Gly Tyr
        130                 135                 140

Tyr Ser Ala Asn Ala Val Thr Val Ala Ile His Gln Gln Ile Pro Ala
145                 150                 155                 160

Gly Arg Asp Tyr His Gly Pro Pro Leu Pro Tyr Gly Tyr Leu His Cys
                165                 170                 175

Ile Glu Asp Trp Asp Glu Ala Ala Leu Ser Thr Ser Gly Gln Gly Ser
                180                 185                 190

Gly Tyr Val Ala Thr Asp Asp Val Val Arg Val Asp Leu Ser Lys Leu
            195                 200                 205

Thr Trp Leu Asn Asn Lys Thr
        210                 215

<210> SEQ ID NO 5
```

<211> LENGTH: 1659
<212> TYPE: DNA
<213> ORGANISM: Mycobacterium austroafricanum

<400> SEQUENCE: 5

```
gtgacaacat ccgccgatca gaccgacgtt ctggtcatcg gttcgggacc gggcggcgcg      60
ggcgtcacgc tcaagctggt gcaggccgga tacaaggtga cctgcctgga gcagggcct     120
tgggtgacac cgcccgagca cccgcattac accgggaat gggagatcga aaagcaacgc     180
ggatgggcct acgacccgaa cgtccgtgga ctcccggaag actaccggt gaccggcttc     240
accacgcctt atctcatgaa caacgtgggc ggtagcacga tgcactacgc cggccactgg    300
ccgcgctaca agccggtcga cttccgcaag ggcaccgagc acgggttgga aggcacgatc    360
gactggccga tcagctacga agagctcgcg ccgtactacg acgagaacga cgcgatctac    420
ggcatctccg gcatggtggg cgatccgtcg tatccggatc gaaccggagt cgaccgcgat    480
ccaccggtca aacgggcaa gctggggcgc aacttcgctc aggcgctggg cgacctgggt    540
tggcactggt ggccatcgga caacgcgatc atcactcggc cacgcgaagg ccgcgaggct    600
gacatcgccg caggcaacga gctctcgggt agcccgacgg gatcgctcag cacgccgacg    660
cacacccact ggccgaccgc catcgcgctc ggagcggact tgcgtaccca cgcccgagtc    720
gaacagatcc acacgaagaa cggcaaggcc accggtgcga cctacatcga cacccgtacc    780
ggcgcacggc acgagatcaa cgcgaagatc gtggtggtct cggccagcgg gatcggaacc    840
ccgagactgc tcctcatgag cgcgcagaag gggcatcccg acggtctggc caacagcaac    900
ggtctcgtcg gcaaatacct gatgcaccac attcttcgcg ttctggcgag cgtggttcgc    960
acaagccgga tggaaggcta caagggagcc ttcggcgctc cactgtattc gcacgagttc   1020
taccacaccg acaccaatcg cggcttcgtc aacggttcg gcatgcaggt ggcacgcagc   1080
ttcggcgctg catacacagc aatgggcagc cacaccggtt acgtggcccc ctggggcaaa   1140
tcgcatcgca agttcttcaa cgaacacttc ggcaatcact tgatggtttt catgttcggc   1200
gaagacctcc ccgtcgagac gaactgcgtg acactcgatc ctgacgccaa agactcgagt   1260
ggcctccctg cggcgcgtgt caactgggaa ccacacgaga cgacatcgc gctggccaat   1320
tacggcatcg accggatctt cgaggccgcg cgagcgttgg gcgctgtcga gaccaacgac   1380
accggcgtgc tcaatcctcc gcccggttgg cacttgatgg gcacctgtcg gatgggtaac   1440
aacccagaag attcggtcac caacaagtgg catcagacct gggatgtgcc gaatctcttc   1500
gttgtcgacg ggagctcgct caccaccggc ggagctgtca acccgacatc gacgatcggc   1560
gcgctcgccg tgcgggcagg agattacatc tcccgccgat tctccgacat cgtcgatcag   1620
cgcaccacgc cgagcaacga agacgcacct gccatctaa                          1659
```

<210> SEQ ID NO 6
<211> LENGTH: 552
<212> TYPE: PRT
<213> ORGANISM: Mycobacterium austroafricanum

<400> SEQUENCE: 6

```
Met Thr Thr Ser Ala Asp Gln Thr Asp Val Leu Val Ile Gly Ser Gly
 1               5                  10                  15

Pro Gly Gly Ala Gly Val Thr Leu Lys Leu Val Gln Ala Gly Tyr Lys
            20                  25                  30

Val Thr Cys Leu Glu Gln Gly Pro Trp Val Thr Pro Pro Glu His Pro
        35                  40                  45
```

His Tyr His Arg Glu Trp Glu Ile Glu Lys Gln Arg Gly Trp Ala Tyr
       50                  55                  60

Asp Pro Asn Val Arg Gly Leu Pro Glu Asp Tyr Pro Val Thr Gly Phe
 65                  70                  75                  80

Thr Thr Pro Tyr Leu Met Asn Asn Val Gly Gly Ser Thr Met His Tyr
                 85                  90                  95

Ala Gly His Trp Pro Arg Tyr Lys Pro Val Asp Phe Arg Lys Gly Thr
                100                 105                 110

Glu His Gly Leu Glu Gly Thr Ile Asp Trp Pro Ile Ser Tyr Glu Glu
            115                 120                 125

Leu Ala Pro Tyr Tyr Asp Glu Asn Asp Ala Ile Tyr Gly Ile Ser Gly
        130                 135                 140

Met Val Gly Asp Pro Ser Tyr Pro Asp Arg Thr Gly Val Asp Arg Asp
145                 150                 155                 160

Pro Pro Val Lys Pro Gly Lys Leu Gly Arg Asn Phe Ala Gln Ala Leu
                165                 170                 175

Gly Asp Leu Gly Trp His Trp Trp Pro Ser Asp Asn Ala Ile Ile Thr
            180                 185                 190

Arg Pro Arg Glu Gly Arg Glu Ala Asp Ile Ala Ala Gly Asn Glu Leu
        195                 200                 205

Ser Gly Ser Pro Thr Gly Ser Leu Ser Thr Pro Thr His Thr His Trp
210                 215                 220

Pro Thr Ala Ile Ala Leu Gly Ala Asp Leu Arg Thr His Ala Arg Val
225                 230                 235                 240

Glu Gln Ile His Thr Lys Asn Gly Lys Ala Thr Gly Ala Thr Tyr Ile
                245                 250                 255

Asp Thr Arg Thr Gly Ala Arg His Glu Ile Asn Ala Lys Ile Val Val
            260                 265                 270

Val Ser Ala Ser Gly Ile Gly Thr Pro Arg Leu Leu Leu Met Ser Ala
        275                 280                 285

Gln Lys Gly His Pro Asp Gly Leu Ala Asn Ser Asn Gly Leu Val Gly
    290                 295                 300

Lys Tyr Leu Met His His Ile Leu Arg Val Leu Ala Ser Val Val Arg
305                 310                 315                 320

Thr Ser Arg Met Glu Gly Tyr Lys Gly Ala Phe Gly Ala Pro Leu Tyr
                325                 330                 335

Ser His Glu Phe Tyr His Thr Asp Thr Asn Arg Gly Phe Val Asn Gly
            340                 345                 350

Phe Gly Met Gln Val Ala Arg Ser Phe Gly Ala Ala Tyr Thr Ala Met
        355                 360                 365

Gly Ser His Thr Gly Tyr Val Ala Pro Trp Gly Lys Ser His Arg Lys
370                 375                 380

Phe Phe Asn Glu His Phe Gly Asn His Leu Met Val Phe Met Phe Gly
385                 390                 395                 400

Glu Asp Leu Pro Val Glu Thr Asn Cys Val Thr Leu Asp Pro Asp Ala
                405                 410                 415

Lys Asp Ser Ser Gly Leu Pro Ala Ala Arg Val Asn Trp Glu Pro His
            420                 425                 430

Glu Asn Asp Ile Ala Leu Ala Asn Tyr Gly Ile Asp Arg Ile Phe Glu
        435                 440                 445

Ala Ala Arg Ala Leu Gly Ala Val Glu Thr Asn Asp Thr Gly Val Leu
450                 455                 460

Asn Pro Pro Pro Gly Trp His Leu Met Gly Thr Cys Arg Met Gly Asn

```
                465                 470                 475                 480
Asn Pro Glu Asp Ser Val Thr Asn Lys Trp His Gln Thr Trp Asp Val
                    485                 490                 495

Pro Asn Leu Phe Val Val Asp Gly Ser Ser Leu Thr Thr Gly Gly Ala
            500                 505                 510

Val Asn Pro Thr Ser Thr Ile Gly Ala Leu Ala Val Arg Ala Gly Asp
        515                 520                 525

Tyr Ile Ser Arg Arg Phe Ser Asp Ile Val Asp Gln Arg Thr Thr Pro
    530                 535                 540

Ser Asn Glu Asp Ala Pro Ala Ile
545                 550

<210> SEQ ID NO 7
<211> LENGTH: 672
<212> TYPE: DNA
<213> ORGANISM: Mycobacterium austroafricanum

<400> SEQUENCE: 7
atgtcggcaa ccgacgtccc gccgcttccc caatccatcg gcccactgca cccggacgtt    60
gaagccggca gcttgtccga accaggtctc gagaccgcgg cgggccgctg ggtagctttc   120
ggcctggcca atctggcggt ggtgctggca gtgtccttgg cggggtggta cctgctcgcc   180 gaccccgac tcagcccgtg gtccttctat ccactcccgt tcaacgcggc tctgttctgg    240
gccatcctct tcgttgtgtt catcggcttc aatgccggat tcgcagggtt catccgactt   300
tcacagccat ggcggggact cgccatcacc gtcgccacgg catcttcgc ggtcgccgtg    360 acgtgggtgc tggcagccgg actcggcagt gtgaacgctg atttcgctgc cggccgagac   420
ggcggcctcg gctacttcac cggcgcgctg ttcgtgctct tcgggttcgg taccttcgtg   480
atagtcgtcc tcaattggca gcactggcca tggccccaac tcggtctctc gcagcccggc   540
gtgggattgg ccgagatcgc gcgcggttgcc ggcccgacca tgctgctgta cttcgccttc   600
ggcttgcccg cagtcagcgc aggcggtgcc gaacccgtgt tggaattgga caccctcatg   660
ggctggttct ag                                                        672

<210> SEQ ID NO 8
<211> LENGTH: 223
<212> TYPE: PRT
<213> ORGANISM: Mycobacterium austroafricanum

<400> SEQUENCE: 8

Met Ser Ala Thr Asp Val Pro Pro Leu Pro Gln Ser Ile Gly Pro Leu
1               5                   10                  15

His Pro Asp Val Glu Ala Gly Ser Leu Ser Pro Gly Leu Glu Thr
                20                  25                  30

Ala Ala Gly Arg Trp Val Ala Phe Gly Leu Ala Asn Leu Ala Val Val
            35                  40                  45

Leu Ala Val Ser Leu Ala Gly Trp Tyr Leu Leu Ala Asp Pro Arg Leu
        50                  55                  60

Ser Pro Trp Ser Phe Tyr Pro Leu Pro Phe Asn Ala Ala Leu Phe Trp
65                  70                  75                  80

Ala Ile Leu Phe Val Val Phe Ile Gly Phe Asn Ala Gly Phe Ala Gly
                85                  90                  95

Phe Ile Arg Leu Ser Gln Pro Trp Arg Gly Leu Ala Ile Thr Val Ala
            100                 105                 110

Thr Gly Ile Phe Ala Val Ala Val Thr Trp Val Leu Ala Ala Gly Leu
```

```
                      115                 120                 125
Gly Ser Val Asn Ala Asp Phe Ala Ala Gly Arg Asp Gly Gly Leu Gly
    130                 135                 140

Tyr Phe Thr Gly Ala Leu Phe Val Leu Phe Gly Phe Gly Thr Phe Val
145                 150                 155                 160

Ile Val Val Leu Asn Trp Gln His Trp Pro Trp Pro Gln Leu Gly Leu
                165                 170                 175

Ser Gln Pro Gly Val Gly Leu Ala Glu Ile Ala Ala Val Ala Gly Pro
            180                 185                 190

Thr Met Leu Leu Tyr Phe Ala Phe Gly Leu Pro Ala Val Ser Ala Gly
        195                 200                 205

Gly Ala Glu Pro Val Leu Glu Leu Asp Thr Leu Met Gly Trp Phe
    210                 215                 220
```

<210> SEQ ID NO 9
<211> LENGTH: 1233
<212> TYPE: DNA
<213> ORGANISM: Mycobacterium austroafricanum

<400> SEQUENCE: 9

```
tcagtcttgt tgacctatag cgctcagtgt tgtgcgcagt gcccgcactg cgggcgctac      60
cgatggcgcc aacaaacctg ccatgttcgc tggatagcgg acggtcacga cggcgggttc     120
ggcgaaccga tagggtcgac ccaccacgat gcccgcgaat tgctttctga gtcgggacat     180
ctccactcga acggctccaa cgcgtgtggc gtctccgtac aggtctgccg caagcgcagg     240
cgcagagcgg ccgtcagcgc tgtgggccag tatgagcagt atctcggcgt gccgcagtga     300
aatgtcgtgc cgccagttac cgaatcggcc ctccatctcg agcgcaggag aggcactgtc     360
gtgcagattc aacgtgaccc gtgtgactgc tgactccgtg tcgcttccca ccagtcgcac     420
caaccacccg ccgggtagca tctcgacctc gcaatcgccg agtgacggca cccataagtg     480
gccgggcgcg atatcggcgg gcagcatgat ccgcctctgc acggtcaacg agtccactgc     540
ggccacccaa ccgtccccat ccacggccac ggcaggcgac ccgactcgcg ccagtatcgg     600
agcagcgacc gagcgcagcc ggttcagtgc gagttcgtgc tgcccacgca actccgattc     660
ggccaaccgt gccacggcgt cgatgagggc gaccgtcacc ggatgcacgg tcgccgccgg     720
tccggtcacg tcgaccacac cgatcacgcg gccggtgcgc ggactacgga tcggtgcgcc     780
cgcgcacgtc cacgggtgtt ggctgcggtt gtaatgctcc gcactgaagg tctggacggc     840
gcgctgtgag acgagagcgg taccgagggc gttcgtaccg accgtcgttt cggcccactg     900
ggctccttcg acgaacccaa gcctgtccgc gttcgccagc acacgaggcg agccggatcg     960
ccacagcaca gcgcactcgg catcggcgac ggcaacgata ctgtcgcccg tggacgtcaa    1020
cggggcgagg ccgcgcgtca actccccgac caccgaagcc aagccggatt cggacctcaa    1080
cacctcgacc gtgtccgact ccatcacggg cggcggtcga cggtcgggtc gcaaaccct    1140
ggccatgagt cgctgccagg aatcccagat gacacgacgt ggacgggccg gagcttgccc    1200
gcccgccatc gtggcctcgt agacagccgc cat                                 1233
```

<210> SEQ ID NO 10
<211> LENGTH: 410
<212> TYPE: PRT
<213> ORGANISM: Mycobacterium austroafricanum

<400> SEQUENCE: 10

Met Ala Ala Val Tyr Glu Ala Thr Met Ala Gly Gly Gln Ala Pro Ala

```
1               5                   10                  15

Arg Pro Arg Arg Val Ile Trp Asp Ser Trp Gln Arg Leu Met Ala Arg
                20                  25                  30

Gly Leu Arg Pro Asp Arg Arg Pro Pro Val Met Glu Ser Asp Thr
            35                  40                  45

Val Glu Val Leu Arg Ser Glu Ser Gly Leu Ala Ser Val Val Gly Glu
        50                  55                  60

Leu Thr Arg Gly Leu Ala Pro Leu Thr Ser Thr Gly Asp Ser Ile Val
65                      70                  75                  80

Ala Val Ala Asp Ala Glu Cys Ala Val Leu Trp Arg Ser Gly Ser Pro
                    85                  90                  95

Arg Val Leu Ala Asn Ala Asp Arg Leu Gly Phe Val Glu Gly Ala Gln
                100                 105                 110

Trp Ala Glu Thr Thr Val Gly Thr Asn Ala Leu Gly Thr Ala Leu Val
            115                 120                 125

Ser Gln Arg Ala Val Gln Thr Phe Ser Ala Glu His Tyr Asn Arg Ser
        130                 135                 140

Gln His Pro Trp Thr Cys Ala Gly Ala Pro Ile Arg Ser Pro Arg Thr
145                 150                 155                 160

Gly Arg Val Ile Gly Val Val Asp Val Thr Gly Pro Ala Ala Thr Val
                165                 170                 175

His Pro Val Thr Val Ala Leu Ile Asp Ala Val Ala Arg Leu Ala Glu
                180                 185                 190

Ser Glu Leu Arg Gly Gln His Glu Leu Ala Leu Asn Arg Leu Arg Ser
            195                 200                 205

Val Ala Ala Pro Ile Leu Ala Arg Val Gly Ser Pro Ala Val Ala Val
        210                 215                 220

Asp Gly Asp Gly Trp Val Ala Val Asp Ser Leu Thr Val Gln Arg
225                 230                 235                 240

Arg Ile Met Leu Pro Ala Asp Ile Ala Pro Gly His Leu Trp Val Pro
                245                 250                 255

Ser Leu Gly Asp Cys Glu Val Glu Met Leu Pro Gly Gly Trp Leu Val
            260                 265                 270

Arg Leu Val Gly Ser Asp Thr Glu Ser Ala Val Thr Arg Val Thr Leu
        275                 280                 285

Asn Leu His Asp Ser Ala Ser Pro Ala Leu Glu Met Glu Gly Arg Phe
    290                 295                 300

Gly Asn Trp Arg His Asp Ile Ser Leu Arg His Ala Glu Ile Leu Leu
305                 310                 315                 320

Ile Leu Ala His Ser Ala Asp Gly Arg Ser Ala Pro Ala Leu Ala Ala
                325                 330                 335

Asp Leu Tyr Gly Asp Ala Thr Arg Val Gly Ala Val Arg Val Glu Met
            340                 345                 350

Ser Arg Leu Arg Lys Gln Phe Ala Gly Ile Val Val Gly Arg Pro Tyr
        355                 360                 365

Arg Phe Ala Glu Pro Ala Val Val Thr Val Arg Tyr Pro Ala Asn Met
    370                 375                 380

Ala Gly Leu Leu Ala Pro Ser Val Ala Pro Val Arg Ala Leu Arg
385                 390                 395                 400

Thr Thr Leu Ser Ala Ile Gly Gln Gln Asp
                405                 410

<210> SEQ ID NO 11
```

-continued

```
<211> LENGTH: 10327
<212> TYPE: DNA
<213> ORGANISM: Mycobacterium austroafricanum

<400> SEQUENCE: 11
tgcagcacag cacccgcacc ccaccggcgg cgatacctcg ccacccggct cacccgcgcg      60
gtaggcaccc accgcaacaa cacgggcaga gcggtccagc acctgtggag aatcatcgac     120
accctcaccg actaccttcg cgccgtcgac agcggtcacc gcacctacac cgaagcgttc     180
cacgaactgc tgccctacta cgccgacgca tcacaagccg ttgggactgc gaccaatccg     240
gcctgacgac atgaccaacc cgggacatat gggcgccgaa tcgggcgttt cgccgacagc     300
ccacggcacc ctcaaggcgt ccttctgacc caaccgaagt gcagcctatt cacctgaatg     360
acagcggcgc ctattgttgg acacatggtg tcggctacac ctcacgagtc ccgctcggtc     420
actgcgcaac gctcgtcggg tgacgaacag cgcctcgacg ccgcgtatgc ggaactggcc     480
acgtcgttca acgaagaagt caccgacgcc gagagacgcg cggcgcgcac caagtacatc     540
gaccgccgcg aacccggccg tcaatgaatg cggcgcgcat cttgtcgtcg gccttctcat     600
atcaagtatc gaatggtcac acagggcgcg gcgaccggtg gggccgtccc atgggcactt     660
cccggcttcc ttcgaccact cgccacgggg ccggcaggac gtcgcctcga cgcgccaact     720
caaatgacgc tgccaatcac aagcccatct caccgacgct ggcggtccta tgcatcgggt     780
caccaggtcg actgagaacg gacaaagtgg gtccggattg gtcgacgaac tgcgcgaggc     840
cggctgcgcc gtgggtgtag tgaagggccg cacccacggc gctgatcaag acagaccgta     900
gcggcgtcgc agctcctcgc cgctgatcgt gttccccgcc gcataatccg catccgcggc     960
ggccagttca tcgactaacc gctcattggc agcatggatt gcatcagcca atgctgcgaa    1020
gtcggccggc gtgctgccag caggatcgtc actcatggct ccattctcgt cacaaccgac    1080
tcgcccgtgg cgcgacggat ggacccgagc gcggcgatc cgctccaact cttttagcga    1140
cagcacgtag tccgctagtt agtattggcg gtcgcgctgg cctcgatgcc gcggtgttcg    1200
ccgagcatcc gcttgtaggt gtgttacggt ttggcgattt gtctcactgt ttttgtgatc    1260
tctgtttcga cctgagccgc ctcttgaatt tgttcggtaa gcgatcggtc ggccaactgg    1320
gtgtttctgt tcgcatgtct gcatattgtt cctattcatg caccactgat tactcttgtg    1380
gagaataagc gtgtcggtcc caacatgtat tatctgaacg gtgagtagag aaagagcggc    1440
gcttaagcct tgctgactac agcgtgccaa agacgcctct agtacgcgcg attgcttaac    1500
cggaaccgta cccagccgcg cacccgcacg gcagtccgcc acgcggctc cctgaacaat    1560 caccccaccg aggctgaaaa gctccggag tcgataaaca gatttgtcag tcagtccaag    1620
ctattcgaaa gcaacgtcgt gcctagtctc gctgatactt tggcgaagat ccaacagaca    1680
acgatgcaaa gcttgcgccc gatctacgtc ccgcagctgc ccgaatcgat gttcgacagc    1740
cttcgcaaga ccttaaaggg catctttccc gctaattggc cgagcgaatt gcctgacttc    1800
gaccgcatcg aggaggtcat agagaaggac ggcatcccta tcgtccacat cccgcgagct    1860
gagatcgtcc aagagatctg cgacgctcac gactacgacg cacgcgtgca aatcttggtc    1920
gaccgtgcaa gcgacatcgc tgacgattgc cgagatgcac ttcagcgtgt ctacgacgag    1980
atagtggata gcagctcccc ctagcccag cgagcgatcg aggcatacca ggctggatac    2040
ttcgagtctg cccaggcatt ggcggtgagt gtgtgcgata cctatctgaa gaagatgtat    2100
caaggcacgc gctatgcgga catacaaagt gatctcacgc tcgataactc gaacgaggtg    2160
gccgtcgccg tcgccttcaa cttttcacttc gcattggcat ccgcagttcc gttcctcacc    2220
```

```
ccctggaacc ctgcgagggg tgaaaagccg cccacgaggc tgtcacgcac gcgagtatcc    2280
atgacgcaag caccgaccat atgacgctgc tgaatgcgac gattgcgata atgctcctga    2340
ccagcatgac tgttgctatc gactacatgg ctcggcgcgt gcggaagaac aagggagatt    2400
gcgacacctg aagtcctcgc acgccgcgtg acaggtacgc ctcctctatc cacgtcggcg    2460
aaggcgatcg cttaaccgcg attgcggact tggcaacatc atcaagacgc cctccttcac    2520
ctccgtctca atgcagttgg catcctcaca ggtcgcgagt gacacctcta ctgagaccgg    2580
acaactccgc gcgccgcggc caaccacacc accatcaccg acatcgaagc cgccctgcgc    2640
gaccaacggc tcctgaaccc cgcgcccgca accatcgccg acgccgcacc ctatggcgcc    2700
agctcggtga ctggccacct cacgcgtaca tcacgccggc gactcccgca tcggacgctt    2760
aagtcagtct tgttgaccta tagcgctcag tgttgtgcgc agtgcccgca ctgcgggcgc    2820
taccgatggc gccaacaaac ctgccatgtt cgctggatag cggacggtca cgacggcggg    2880
ttcggcgaac cgatagggtc gacccaccac gatgcccgcg aattgctttc tgagtcggga    2940
catctccact cgaacggctc caacgcgtgt ggcgtctccg tacaggtctg ccgcaagcgc    3000
aggcgcagag cggccgtcag cgctgtgggc cagtatgagc agtatctcgg cgtgccgcag    3060
tgaaatgtcg tgccgccagt taccgaatcg gccctccatc tcgagcgcag gagaggcact    3120
gtcgtgcaga ttcaacgtga cccgtgtgac tgctgactcc gtgtcgcttc ccaccagtcg    3180
caccaaccac ccgccgggta gcatctcgac ctcgcaatcg ccgagtgacg gcacccataa    3240
gtggccgggc gcgatatcgg cgggcagcat gatccgcctc tgcacggtca acgagtccac    3300
tgcggccacc caaccgtccc catccacggc cacggcaggc gacccgactc gcgccagtat    3360
cggagcagcg accgagcgca gccggttcag tgcgagttcg tgctgcccac gcaactccga    3420
ttcggccaac cgtgccacgg cgtcgatgag ggcgaccgtc accggatgca cggtcgccgc    3480
cggtccggtc acgtcgacca caccgatcac gcggccggtg cgcggactac ggatcggtgc    3540
gcccgcgcac gtccacgggt gttggctgcg gttgtaatgc tccgcactga aggtctggac    3600
ggcgcgctgt gagacgagag cggtaccgag ggcgttcgta ccgaccgtcg tttcggccca    3660
ctgggctcct tcgacgaacc caagcctgtc cgcgttcgcc agcacacgag gcgagccgga    3720
tcgccacagc acagcgcact cggcatcggc gacggcaacg atactgtcgc ccgtggacgt    3780
caacggggcg aggccgcgcg tcaactcccc gaccaccgaa gccaagccgg attcggacct    3840
caacacctcg accgtgtccg actccatcac gggcggcggt cgacggtcgg gtcgcaaacc    3900
cctggccatg agtcgctgcc aggaatccca gatgacacga cgtggacggg ccggagcttg    3960
cccgcccgcc atcgtggcct cgtagacagc cgccatcagc cgcgagtagt cgcgcggatg    4020
cctgtccggg cgcgatcgcg ggctccaggt cgggcagtgc tgtgcatcac ctccatcatg    4080
ccctaccgtg ctgcggtcct accacaggaa ccgccaggtg acgcctcgaa ttcaggagta    4140
cgcccggcgc tgtaacgccc gtgtaactct tgcgggcgca cccctcgtga atgtgtgctg    4200
cttcacacga acggccgtac atgccgctcg tcacagcggt cggaacagac agtgacctgc    4260
ctgtccggcg gccgggcccg cctcggtgaa tcaccgaccc ggcacgcgag tcattcatag    4320
gagcgagaac aacatgaccc gaactctctc ggctgatgcc gacacccgca cggcgacacc    4380
tccgctgatg tacgtcaacg gcgagtggct gcccgcccgc agtggggcca cctttcccac    4440
catcgaaccc agcacgggtc gaccgatcac tgagattccc cgcggggact cgagcgatgt    4500
ggacgcggcg gtgaaagccg ctgccgacgt ggccgttgag tggcagttca ccgatgccat    4560
```

```
cacccgcgcc gccctgctca ggcgattggc ggagctggtg gcagagaacg ccgaggagct    4620
ggcgcggatc gagtcgctgg actcgggtca ctatctggcg aaggcgcgtg aactggtgac    4680
cgcgataccc ctgtggctcg agtactgggc cggcgcagct gacaaagtgg gcggccgcac    4740
catcgctgta ccgggtaaca aactcagctt caccttgttg gaaccgctgg gcgtcaccgc    4800
gcacatcatc ccgtggaact acccgctgtt gatccttgct cggtccatcg ccccggcact    4860
cgcattgggc aacacctgtg tcgtcaagcc cgctgaggac acgtccctgt cagcgctgaa    4920
gttcgccgag ctggtacacg ccgccggttt cccgccgga gtgttcaatg tggtgaccgg     4980
ttacggttcc gaagccggcg cggctcttgc cgctcacccc gaggtgcgcg gaatcacctt    5040
caccggttcg accgagaccg ggcgggagat cgcccgactg gcggccaac acatcgccca     5100 ggtcaacctg gaactcggcg ggaagagccc gttggtcgtc tttcccgacg cgccgctcga    5160
agacgccgta gaggtggccg tacagggctt ctgctcacgg gcagggcaag tgtgtgtcgc    5220
cgggagccgc ctcttcctcc atgaggacat cgccgaccgg ttcctcgaga tgctcgtttc    5280
gcgactcgag actgtcaccg tcggcgaccc gttcgacggt gcgacccaga tgggtccgct    5340
cgcctcgaag aagcactacg accgtgtgcg tgagtacatc gaggtcggga agcaggaggc    5400
gaccctgctc tacggcggcg gtcggccgac ggacacgccc gatgacgggt tcttcgtcga    5460
gccaacggtt ttcgtcgacg tcgcaacgga tgcgcggatc gcacgcgagg agatcttcgg    5520
gcccgtcaca gcggtgatgc ggtggtcatc ggtcgacgat ctgatcgcca ccatcaatga    5580
ttcggaattc ggtctcttcg ctgtgctctg gtgccgggac atcaccagtg cgctggacac    5640
ggcgaaacgc ctgcaggtcg gctcggtaat gatcaacgac tggttcggtg agctgccgat    5700
gactccgcac ggaggccaca agcaaagcgg caccggacgc gaggaaggcc tcgaagcggt    5760
acacggctac acacaggtca agcacatcgg catcaacctc gagccgtcgc ccgcaaagtc    5820
cgccgattgg gccggtgcac ctctgtgatc gatcggccgc ttgccgtgcg gtgctgaaca    5880
acgcattcca agaacaacac acatgaagga gagtcaatgc ctcaagaaga cgccttggtg    5940
agcgccccat tcggggcgcc gtccttgggg gaagatcgtc ccgatcaacc ccatttcgag    6000
accggccgac cgagactcgg cggactggtc gccccgtcg cgtttgatga gctcgaggca     6060
gcggtcatcg acgccctggc cgacacgatg atccccgccg aaggcggctt ccgccgca      6120 agcgacgtgg gaatcgtcga tttcttcggc cgctacacga ctcccaccgg attccgcgcg    6180
aagcacttcc cctacctcga agaggacaag ttgaagagcg cactcgcggg gctcggcgaa    6240
gaattcgtca acgccgacac cgatacgcgc acccaggcgg tcctccgatt ggagaaggac    6300
gatgaggagt tcttcgcgca ggtgagaagc ctcgtgtatt acggctacta ctccgcgaac    6360
gcagtgaccg tcgccattca ccagcagatt ccggccgggc gcgactacca cggacccca     6420 ctcccctacg gctatctgca ttgcatcgag gactgggatg aagcggcgct ctccacatcg    6480
gggcagggct caggctatgt cgccaccgac gatgtggtcc gagtggatct cagcaaactc    6540
acctggctga caacaagac ttgaacacaa gacttgacga ggagcacaag tgacaacatc     6600
cgccgatcag accgacgttc tggtcatcgg ttcgggaccg gcggcgcgg gcgtcacgct     6660 caagctggtg caggccggat acaaggtgac ctgcctggag caggggcctt gggtgacacc    6720
gcccgagcac ccgcattacc accgggaatg ggagatcgaa aagcaacgcg gatgggccta    6780
cgacccgaac gtccgtggac tcccggaaga ctacccggtg accggcttca ccacgcctta    6840
tctcatgaac aacgtgggcg gtagcacgat gcactacgcc ggccactggc cgcgctacaa    6900
gccggtcgac ttccgcaagg gcaccgagca cgggttggaa ggcacgatcg actggccgat    6960
```

```
cagctacgaa gagctcgcgc cgtactacga cgagaacgac gcgatctacg gcatctccgg    7020
catggtgggc gatccgtcgt atccggatcg aaccggagtc gaccgcgatc caccggtcaa    7080
accgggcaag ctggggcgca acttcgctca ggcgctgggc gacctggatt ggcactggtg    7140
gccatcggac aacgcgatca tcactcggcc acgcgaaggc cgcgaggctg acatcgccgc    7200
aggcaacgag ctctcgggta gcccgacggg atcgctcagc acgccgacgc cacccactg    7260 gccgaccgcc atcgcgctcg gagcggactt gcgtacccac gcccgagtcg aacagatcca    7320
cacgaagaac ggcaaggcca ccggtgcgac ctacatcgac acccgtaccg cgcacggca    7380 cgagatcaac gcgaagatcg tggtggtctc ggccagcggg atcggaaccc cgagactgct    7440
cctcatgagc gcgcagaagg ggcatcccga cggtctggcc aacagcaacg gtctcgtcgg    7500
caaatacctg atgcaccaca ttcttcgcgt tctggcgagc gtggttcgca caagccggat    7560
ggaaggctac aagggagcct tcggcgctcc actgtattcg cacgagttct accacaccga    7620
caccaatcgc ggcttcgtca acggtttcgg catgcaggtg gcacgcagct cggcgctgc    7680 atacacagca atgggcagcc acaccggtta cgtggccccc tggggcaaat cgcatcgcaa    7740
gttcttcaac gaacacttcg gcaatcactt gatggttttc atgttcggcg aagacctccc    7800
cgtcgagacg aactgcgtga cactcgatcc tgacgccaaa gactcgagtg gcctccctgc    7860
ggcgcgtgtc aactgggaac cacacgagaa cgacatcgcg ctggccaatt acggcatcga    7920
ccggatcttc gaggccgcgc gagcgttggg cgctgtcgag accaacgaca ccggcgtgct    7980
caatcctccg cccggttggc acttgatggg cacctgtcgg atgggtaaca acccagaaga    8040
ttcggtcacc aacaagtggc atcagacctg ggatgtgccg aatctcttcg ttgtcgacgg    8100
gagctcgctc accaccggcg gagctgtcaa cccgacatcg acgatcggcg cgctcgccgt    8160
gcgggcagga gattacatct cccgccgatt ctccgacatc gtcgatcagc gcaccacgcc    8220
gagcaacgaa gacgcacctg ccatctaatc cattcgaact gccgatccac ctcccgcggg    8280
cggcgggagg tggatcggtg tccatttgat ctcttcgagc ccacaggagc accccagatg    8340
tcggcaaccg acgtcccgcc gcttccccaa tccatcggcc cactgcaccc ggacgttgaa    8400
gccggcagct tgtccgaacc aggtctcgag accgcggcgg gccgctgggt agctttcggc    8460
ctggccaatc tggcggtggt gctggcagtg tccttggcgg ggtggtacct gctcgccgac    8520
ccccgactca gcccgtggtc cttctatcca ctcccgttca acgcggctct gttctgggcc    8580
atcctcttcg ttgtgttcat cggcttcaat gccggattcg cagggttcat ccgactttca    8640
cagccatggc ggggactcgc catcaccgtc gccacgggca tcttcgcggt cgccgtgacg    8700
tgggtgctgg cagccggact cggcagtgtg aacgctgatt tcgctgccgg ccgagacggc    8760
ggcctcggct acttcaccgg cgcgctgttc gtgctcttcg ggttcggtac cttcgtgata    8820
gtcgtcctca attggcagca ctggccatgg ccccaactcg gtctctcgca gcccggcgtg    8880
ggattggccg agatcgccgc ggttgccggc ccgaccatgc tgctgtactt cgccttcggc    8940
ttgcccgcag tcagcgcagg cggtgccgaa cccgtgttgg aattggacac cctcatgggc    9000
tggttctagc ccgaattttt cgcggaatgt tgcctttggc ggtgtgtaga taagcgaaag    9060
tgcctgtcct gcaagggata attggacttc tctacggttc aaagatcctg acgggaaggc    9120
acttcgcagg tgaagaatat cgcggccgca tcgcgggtga agtgtcggc cgacggccat    9180 ggcgtcgtgt cgcatgccgg gatgggcctg ctacgtgaac tggccgatcg accgggtta    9240 tcggcgcagg tcacggctgc tttggccgac acctaccgcg ggccgtgggt gtatgcgccc    9300
```

```
ggagacgtgt tcgctgatct ggcggctgcg gttgctgacg gggcggactg catcgacggg    9360
gtcggccagc tctgcggcga ccgtgagcac gccttcggtg cgaaagcctc gacgaccacg    9420
atgtggcggc tggtcgatga gcgcatcgac gccgcacacc tacccgcggt gcgggcggcc    9480
cgagcgggcg cgcgggcggc ggcctgggcc gccggtgccg ccccgctcc gggtgactgg      9540 ctgcacatcg acatcgacgc cacctgtg atcgatcact ccgacaacaa aggcggtgcg     9600
acgccgacct ggaagaagtc gttcgggcac catccgctgc tggcatttct ggaccgcccc    9660
gagatcgccg cggggaagc cctggccggg ctgctacgca ccggcaacgc cggctccaac      9720
accgccagcg accacgtcat cgtgctggcc aagcgctgg cagcgctgcc cgcggcctgg      9780
cgacccgacc ccagggctgg cgatcatccc gacaagccca aggtgctggt gcgctgcgac    9840
accgccggag ccaccacac cttcgccgac gcctgccggg ccgccggggt ggggttctcc     9900
ttcggttacc ccgtcgactg gcgcgtccaa gacgcggtgg acaccctcaa cctcgccgag    9960
ggctggtacc cggcgatcgg caccgccggc ggtctccgcg acgcgcctg gatcgccgaa     10020 gccaccaccc tggtcaacct gtcgtcgtgg ccaccgggca cgcggctgat cctgcgcaaa    10080
gaaaggccgc atccgggcgc ccagctgcga ttcaccgacg ccgacgggat gcggatcaca    10140
gcgttcatca ccgacacacc acccggcgtc gtgtcaggac aggtcgccgg cctggaactg    10200
cgccaccgtc agcacgcccg cgtcgaagac cgcatccgcg aactcaaagc caccggcctg    10260
cgcaacctgc cctgccactc attttgggcc aacgccgcat ggctggaaat cgccctcacc    10320
gccgccg                                                              10327
```

<210> SEQ ID NO 12
<211> LENGTH: 1480
<212> TYPE: DNA
<213> ORGANISM: Mycobacterium austroafricanum

<400> SEQUENCE: 12

```
agagtttgat tctggctcag gacgaacgct ggcggcgtgc ttaacacatg caagtcgaac      60
ggaaaggccc ttcggggtac tcgagtggcg aacgggtgag taacacgtgg gtgatctgcc    120
ctgcactttg ggataagcct gggaaactgg gtctaatacc gaatacaccc ttctggctgc    180
atggtctggt tggggaaagc ttttgcggtg tgggatgggc ccgcggccta tcagcttgtt    240
ggtgaggtta cggctcacca aggcgacgac gggtagccgg cctgagaggg tgaccggcca    300
cactgggact gagatacggc ccagactcct acgggaggca gcagtgggga atattgcaca    360
atgggcgcaa gcctgatgca gcgacgccgc gtgagggatg acggccttcg ggttgtaaac    420
ctctttcgcc agggacgaag cgcaagtgac ggtacctgga gaagaaggac cggccaacta    480
cgtgccagca gccgcggtaa tacgtagggt ccgagcgttg tccggaatta ctgggcgtaa    540
agagctcgta ggtggtttgt cgcgttgttc gtgaaaactc acagctcaac tgtgggcgtg    600
cgggcgatac gggcagactg gagtactgca ggggagactg gaattcctgg tgtagcggtg    660
gaatgcgcag atatcacgag gaacaccggt ggcgaaggcg ggtctctggg cagtaactga    720
cgctgaggag cgaaagcgtg gggagcgaac aggattagat accctggtag tccacgccgt    780
aaacggtggg tactaggtgt gggtttcctt ccttgggatc cgtgccgtag ctaacgcatt    840
aagtaccccg cctggggagt acggccgcaa ggctaaaact caaagaaatt gacggggggcc    900 cgcacaagcg gcggagcatg tggattaatt cgatgcaacg cgaagaacct tacctgggtt    960
tgacatgcac aggacgtgcc tagagatagg tattcccttg tggcctgtgt gcaggtggtg    1020
catggctgtc gtcagctcgt gtcgtgagat gttgggttaa gtcccgcaac gagcgcaacc    1080
```

```
cttatcttat gttgccagcg cgtaatggcg gggactcgtg agagactgcc ggggtcaact    1140
cggaggaagg tggggatgac gtcaagtcat catgcccctt atgtccaggg cttcacacat    1200
gctacaatgg ccggtacaaa gggctgcgat gccgtgaggt ggagcgaatc ctttcaaagc    1260
cggtctcagt tcggatcggg gtctgcaact cgaccccgtg aagtcggagt cgctagtaat    1320
cgcagatcag caacgctgcg gtgaatacgt tcccgggcct tgtacacacc gcccgtcacg    1380
tcatgaaagt cggtaacacc cgaagccggt ggcctaaccc cttgtgggag ggagccgtcg    1440
aaggtgggat cggcgattgg gacgaagtcg taacaaggta                          1480
```

<210> SEQ ID NO 13
<211> LENGTH: 1362
<212> TYPE: DNA
<213> ORGANISM: Mycobacterium austroafricanum

<400> SEQUENCE: 13

```
tcgaacggaa aggcccttcg gggtactcga gtggcgaacg ggtgagtaac acgtgggtga     60
tctgccctgc actttgggat aagcctggga aactgggtct aataccgaat acacccttct    120
ggctgcatgg tctggttggg gaaagctttt gcggtgtggg atgggcccgc ggcctatcag    180
cttgttggtg aggttacggc tcaccaaggc gacgacgggt agccggcctg agagggtgac    240
cggccacact gggactgaga tacggcccag actcctacgg gaggcagcag tggggaatat    300
tgcacaatgg gcgcaagcct gatgcagcga cgccgcgtga gggatgacgg ccttcgggtt    360
gtaaacctct ttcgccaggg acgaagcgca agtgacggta cctggagaag aaggaccggc    420
caactacgtg ccagcagccg cggtaatacg tagggtccga gcgttgtccg gaattactgg    480
gcgtaaagag ctcgtaggtg gtttgtcgcg ttgttcgtga aaactcacag ctcaactgtg    540
ggcgtgcggg cgatacgggc agactggagt actgcagggg agactggaat tcctggtgta    600
gcggtggaat gcgcagatat caggaggaac accggtggcg aaggcgggtc tctgggcagt    660
aactgacgct gaggagcgaa agcgtgggga gcgaacagga ttagataccc tggtagtcca    720
cgccgtaaac ggtgggtact agtgtgtgggt tccttccttt gggatccgtg ccgtagctaa    780
cgcattaagt accccgcctg ggggagtacg ccgccagggc taaaactcaa agaaattgac    840
gggggcccgc acaagcggcg gagcatgtgg attaattcga tgcaacgcga agaaccttac    900
ctgggtttga catgcacagg acgtgcctag agataggtat tcccttgtgg cctgtgtgca    960
ggtggtgcat ggctgtcgtc agctcgtgtc gtgagatgtt gggttaagtc ccgcaacgag   1020
cgcaacccct atcttatgtt gccagcgcgt aatggcgggg actcgtgaga gactgccggg   1080
gtcaactcgg aggaaggtgg ggatgacgtc aagtcatcat gccccttatg tccagggctt   1140
cacacatgct acaatggccg gtacaaaggg ctgcgatgcc gtgaggtgga gcgaatcctt   1200
tcaaagccgg tctcagttcg gatcggggtc tgcaactcga ccccgtgaag tcggagtcgc   1260
tagtaatcgc agatcagcaa cgctgcggtg aatacgttcc cgggccttgt acacaccgcc   1320
cgtcacgtca tgaaagtacg gtaacacccg aagccggtgg ta                      1362
```

<210> SEQ ID NO 14
<211> LENGTH: 591
<212> TYPE: DNA
<213> ORGANISM: Mycobacterium austroafricanum

<400> SEQUENCE: 14

```
acggtctcgt cggcaaatac ctgatgcacc acattcttcg cgttctggcg agcgtggttc     60
```

```
gcacaagccg gatggaaggc tacaagggag ccttcggcgc tccactgtat tcgcacgagt    120
tctaccacac cgacaccaat cgcggcttcg tcaacggttt cggcatgcag gtggcacgca    180
gcttcggcgc tgcatacaca gcaatgggca gccacaccgg ttacgtggcc ccctggggca    240
aatcgcatcg caagttcttc aacgaacact tcggcaatca cttgatggtt ttcatgttcg    300
gcgaagacct ccccgtcgag acgaactgcg tgacactcga tcctgacgcc aaagactcga    360
gtggcctccc tgcggcgcgt gtcaactggg aaccacacga gaacgacatc gcgctggcca    420
attacggcat cgaccggatc ttcgaggccg cgcgagcgtt gggcgctgtc gagaccaacg    480
acaccggcgt gctcaatcct ccgcccggtt ggcacttgat gggcacctgt cggatgggta    540
acaacccaga agattcggtc accaacaagt ggcatcagac ctgggatgtg c             591
```

```
<210> SEQ ID NO 15
<211> LENGTH: 20
<212> TYPE: DNA
<213> ORGANISM: Artificial Sequence
<220> FEATURE:
<223> OTHER INFORMATION: Synthetic Primer

<400> SEQUENCE: 15
tgcacacagg ccacaaccca                                                 20

<210> SEQ ID NO 16
<211> LENGTH: 21
<212> TYPE: DNA
<213> ORGANISM: Artificial Sequence
<220> FEATURE:
<223> OTHER INFORMATION: Synthetic Primer

<400> SEQUENCE: 16
gagagtttga tcctggctca g                                               21

<210> SEQ ID NO 17
<211> LENGTH: 20
<212> TYPE: DNA
<213> ORGANISM: Artificial Sequence
<220> FEATURE:
<223> OTHER INFORMATION: Synthetic Primer

<400> SEQUENCE: 17
cccactgctg cctcccgtag                                                 20

<210> SEQ ID NO 18
<211> LENGTH: 20
<212> TYPE: DNA
<213> ORGANISM: Artificial Sequence
<220> FEATURE:
<223> OTHER INFORMATION: Synthetic Primer

<400> SEQUENCE: 18
accaacgatg gtgtgtccat                                                 20

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer

<400> SEQUENCE: 19
cttgtcgaac cgcataccct                                                 20
```

```
<210> SEQ ID NO 20
<211> LENGTH: 24
<212> TYPE: DNA
<213> ORGANISM: Artificial Sequence
<220> FEATURE:
<223> OTHER INFORMATION: Synthetic Primer

<400> SEQUENCE: 20
gtctaatacc gaatacaccc ttct                                          24

<210> SEQ ID NO 21
<211> LENGTH: 24
<212> TYPE: DNA
<213> ORGANISM: Artificial Sequence
<220> FEATURE:
<223> OTHER INFORMATION: Synthetic Primer

<400> SEQUENCE: 21
gtagttggcc ggtccttctt ctcc                                          24

<210> SEQ ID NO 22
<211> LENGTH: 20
<212> TYPE: DNA
<213> ORGANISM: Artificial Sequence
<220> FEATURE:
<223> OTHER INFORMATION: Synthetic Primer

<400> SEQUENCE: 22
tgagaagcct cgtgtattac                                               20

<210> SEQ ID NO 23
<211> LENGTH: 18
<212> TYPE: DNA
<213> ORGANISM: Artificial Sequence
<220> FEATURE:
<223> OTHER INFORMATION: Synthetic Primer

<400> SEQUENCE: 23
gagataaggc gtggtgaa                                                 18

<210> SEQ ID NO 24
<211> LENGTH: 20
<212> TYPE: DNA
<213> ORGANISM: Artificial Sequence
<220> FEATURE:
<223> OTHER INFORMATION: Synthetic Primer

<400> SEQUENCE: 24
agtgacggca cccataagtg                                               20

<210> SEQ ID NO 25
<211> LENGTH: 21
<212> TYPE: DNA
<213> ORGANISM: Artificial Sequence
<220> FEATURE:
<223> OTHER INFORMATION: Synthetic Primer

<400> SEQUENCE: 25
tcgaggtgtt gaggtccgaa t                                             21

<210> SEQ ID NO 26
<211> LENGTH: 18
<212> TYPE: DNA
<213> ORGANISM: Artificial Sequence
<220> FEATURE:
<223> OTHER INFORMATION: Synthetic Primer
```

-continued

```
<400> SEQUENCE: 26
atcatcccgt ggaactac                                                   18

<210> SEQ ID NO 27
<211> LENGTH: 18
<212> TYPE: DNA
<213> ORGANISM: Artificial Sequence
<220> FEATURE:
<223> OTHER INFORMATION: Synthetic Primer

<400> SEQUENCE: 27
tgacctgggc gatgtgtt                                                   18

<210> SEQ ID NO 28
<211> LENGTH: 18
<212> TYPE: DNA
<213> ORGANISM: Artificial Sequence
<220> FEATURE:
<223> OTHER INFORMATION: Synthetic Primer

<400> SEQUENCE: 28
atcagacctg ggatgtgc                                                   18

<210> SEQ ID NO 29
<211> LENGTH: 19
<212> TYPE: DNA
<213> ORGANISM: Artificial Sequence
<220> FEATURE:
<223> OTHER INFORMATION: Synthetic Primer

<400> SEQUENCE: 29
ggctgtgaaa gtcggatga                                                  19

<210> SEQ ID NO 30
<211> LENGTH: 20
<212> TYPE: DNA
<213> ORGANISM: Artificial Sequence
<220> FEATURE:
<223> OTHER INFORMATION: Synthetic Primer

<400> SEQUENCE: 30
agtgacggca cccataagtg                                                 20

<210> SEQ ID NO 31
<211> LENGTH: 21
<212> TYPE: DNA
<213> ORGANISM: Artificial Sequence
<220> FEATURE:
<223> OTHER INFORMATION: Synthetic Primer

<400> SEQUENCE: 31
tcgaggtgtt gaggtccgaa t                                               21

<210> SEQ ID NO 32
<211> LENGTH: 20
<212> TYPE: DNA
<213> ORGANISM: Artificial Sequence
<220> FEATURE:
<223> OTHER INFORMATION: Synthetic Primer

<400> SEQUENCE: 32
gcaggtcggc tcggtaatga                                                 20

<210> SEQ ID NO 33
<211> LENGTH: 20
```

```
<212> TYPE: DNA
<213> ORGANISM: Artificial Sequence
<220> FEATURE:
<223> OTHER INFORMATION: Synthetic Primer

<400> SEQUENCE: 33
gtaatacacg aggcttctca                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic Primer

<400> SEQUENCE: 34
acggtctcgt cggcaaatac                                               20

<210> SEQ ID NO 35
<211> LENGTH: 18
<212> TYPE: DNA
<213> ORGANISM: Artificial Sequence
<220> FEATURE:
<223> OTHER INFORMATION: Synthetic Primer

<400> SEQUENCE: 35
gcacatccca ggtctgat                                                 18

<210> SEQ ID NO 36
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 36

Lys Gln Arg Gly Trp Ala Tyr Asp Pro Asn Val Arg Gly Leu Pro Glu
1               5                   10                  15

<210> SEQ ID NO 37
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 37

Ser Thr Glu His Gly Leu Glu Gly Thr Ile Asp Trp Pro Ile Ser Tyr
1               5                   10                  15

Glu Glu Leu Ala Pro Tyr Tyr Asp Glu Asn Asp Ala Ile Tyr
            20                  25                  30

<210> SEQ ID NO 38
<211> LENGTH: 17
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
```

```
<222> LOCATION: (12)..(12)
<223> OTHER INFORMATION: y is t or c
<220> FEATURE:
<221> NAME/KEY: misc_feature
<222> LOCATION: (15)..(15)
<223> OTHER INFORMATION: y is t or c

<400> SEQUENCE: 38
ggntgggcnt aygaycc                                                       17

<210> SEQ ID NO 39
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (3)..(3)
<223> OTHER INFORMATION: r is g or a
<220> FEATURE:
<221> NAME/KEY: misc_feature
<222> LOCATION: (6)..(6)
<223> OTHER INFORMATION: r is g or a
<220> FEATURE:
<221> NAME/KEY: misc_feature
<222> LOCATION: (9)..(9)
<223> OTHER INFORMATION: y is t or c
<220> FEATURE:
<221> NAME/KEY: misc_feature
<222> LOCATION: (12)..(12)
<223> OTHER INFORMATION: r is g or a
<220> FEATURE:
<221> NAME/KEY: misc_feature
<222> LOCATION: (15)..(15)
<223> OTHER INFORMATION: s is g or c
<220> FEATURE:
<221> NAME/KEY: misc_feature
<222> LOCATION: (18)..(18)
<223> OTHER INFORMATION: s is g or c

<400> SEQUENCE: 39
gcrtcrttyt crtcstast                                                     19

<210> SEQ ID NO 40
<211> LENGTH: 80
<212> TYPE: PRT
<213> ORGANISM: Artificial Sequence
<220> FEATURE:
<223> OTHER INFORMATION: Synthetic Peptide

<400> SEQUENCE: 40

Lys Gln Arg Gly Trp Ala Tyr Asp Pro Asn Val Arg Gly Leu Pro Glu
1               5                   10                  15

Asp Thr Pro Val Thr Gly Phe Thr Thr Pro Tyr Leu Met Asn Asn Val
            20                  25                  30

Gly Gly Ser Thr Met His Tyr Ala Gly His Trp Pro Arg Tyr Lys Pro
        35                  40                  45

Val Asp Phe Arg Lys Gly Thr Glu His Gly Leu Glu Gly Thr Ile Asp
    50                  55                  60

Trp Pro Ile Ser Tyr Glu Glu Leu Ala Pro Tyr Tyr Asp Lys Asn Asp
65                  70                  75                  80

<210> SEQ ID NO 41
<211> LENGTH: 23
<212> TYPE: DNA
<213> ORGANISM: Artificial Sequence
<220> FEATURE:
<223> OTHER INFORMATION: Synthetic Primer
```

```
<400> SEQUENCE: 41
ttcaccttgt tggaaccgct ggg                                              23

<210> SEQ ID NO 42
<211> LENGTH: 20
<212> TYPE: DNA
<213> ORGANISM: Artificial Sequence
<220> FEATURE:
<223> OTHER INFORMATION: Synthetic Primer

<400> SEQUENCE: 42
tcattaccga gccgacctgc                                                  20
```